United States Patent

Lubisch et al.

[11] Patent Number: 5,849,743
[45] Date of Patent: Dec. 15, 1998

[54] QUINOXALINES AND DRUGS PREPARED THEREFROM

[75] Inventors: Wilfried Lubisch, Mannheim; Berthold Behl; Hans Peter Hofmann, both of Limburgerhof, all of Germany

[73] Assignee: BASF Aktiengesellschaft, Ludwigshafen, Germany

[21] Appl. No.: 860,017

[22] PCT Filed: Dec. 21, 1994

[86] PCT No.: PCT/EP94/03839

§ 371 Date: Jun. 20, 1997

§ 102(e) Date: Jun. 20, 1997

[87] PCT Pub. No.: WO96/19476

PCT Pub. Date: Jun. 27, 1996

[51] Int. Cl.⁶ ............ A61K 31/495; C07D 401/14; C07D 403/04
[52] U.S. Cl. ............ 514/249; 514/250; 544/344; 544/354
[58] Field of Search .................. 544/354, 344; 514/249, 250

[56] References Cited

U.S. PATENT DOCUMENTS 3,992,378  11/1976  St. Clair et al. ............ 544/354

FOREIGN PATENT DOCUMENTS

| 8 864 | 3/1980 | European Pat. Off. . |
| 315 959 | 5/1989 | European Pat. Off. . |
| 374 534 | 6/1990 | European Pat. Off. . |
| 377 112 | 7/1990 | European Pat. Off. . |
| 572 852 | 12/1993 | European Pat. Off. . |
| 91/13878 | 9/1991 | WIPO . |
| 92/07847 | 5/1992 | WIPO . |

OTHER PUBLICATIONS

Lees, *Pharmacology and Pathophysiology* 5, pp. 51–74 (1996).
Lubisch et al., *Chemical Abstracts,* vol. 123, No. 256765 (Abstract for DE 4340045 (Jun. 1, 1995).
Sastry et al Indian J. of Chem. B, 28, 1989–pp. 888–890.
Chem. Abstr. DE 4217952 (May 30, 1992), Lubisch et al.

*Primary Examiner*—Emily Bernhardt
*Attorney, Agent, or Firm*—Keil & Weinkauf

[57] ABSTRACT

Quinoxaline-2,3-(1H,4H)-diones of the formula I

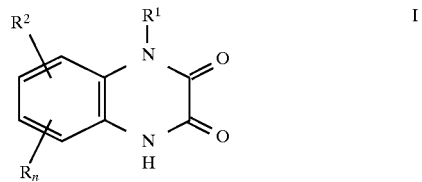

and their tautomeric and enantiomeric forms and their physiologically tolerated salts, the variables R, $R^1$ and $R^2$ have the meanings specified in claim 1, and are useful for therapeutic treatment of neurodegenerative disorders, neurotoxic disturbances or as antiepileptics, antidepressants and anxiolytics; and drugs composed thereof.

4 Claims, No Drawings

QUINOXALINES AND DRUGS PREPARED THEREFROM

The present invention relates to quinoxaline-2,3(1H),4H)-diones of the general formula I

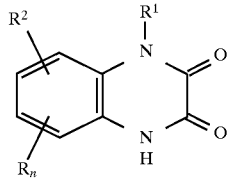

and their tautomeric and enantiomeric forms and their physiologically tolerated salts, where the variables have the following meanings:

$R^1$—hydrogen,
a cycloaliphatic radical having up to 8 carbon atoms,
an aliphatic radical which has 1 to 6 carbon atoms and can carry one or two identical or different substituents phenyl, cyclopentyl, cyclohexyl, —$COR^3$, —CO—O—$R^3$, —CO—NH—$R^3$, $OR^3$,

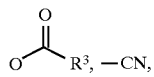

where $R^3$ is hydrogen, $C_1$–$C_4$-alkyl, phenyl, benzyl, 1-phenylethyl or 2-phenylethyl, and where the cycloaliphatic radical or phenyl ring contained in $R^1$ or representing $R^1$ can carry up to three identical or different substituents from the following: $C_1$–$C_4$-alkyl, $C_1$–$C_4$-haloalkyl, $C_1$–$C_4$-alkoxy, $C_1$–$C_4$-haloalkoxy, halogen, nitro, cyano, —CO—$OR^5$, —CO—NH—$R^5$, —OH,

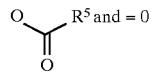

and where $R^5$ has, independently of $R^3$, the same meanings as $R^3$, $R^2$ —a pyrrole group

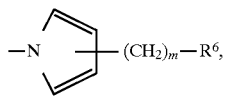

where $R^6$ is one of the following radicals:

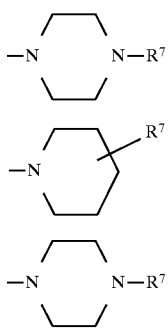

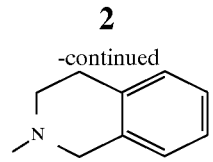

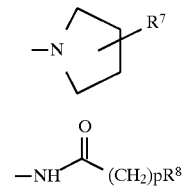

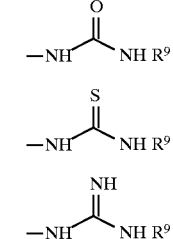

where $R^7$ is hydrogen, branched or linear $C_1$–$C_4$-alkyl which can also carry one or two phenyl rings, and $R^8$ is one of the radicals

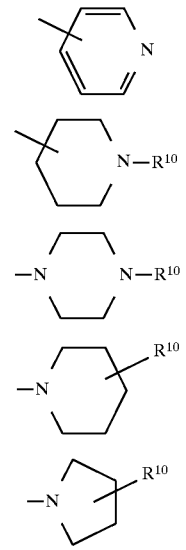

where $R^{10}$ is hydrogen and a branched or linear $C_1$–$C_4$-alkyl which can also carry one or two phenyl rings,
$R^9$ is hydrogen, phenyl, a branched or linear $C_1$–$C_4$-alkyl which can also carry one or two phenyl rings, and

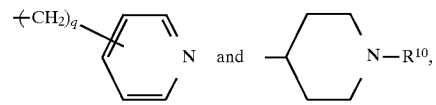

m is an integer from 1 to 4,
p and q are, independently of one another, a number from 0 to 4,
where the phenyl groups present where appropriate in $R^7$, $R^9$ and $R^{10}$, and the pyridine ring representing $R^8$ and $R^9$ where appropriate or present in $R^9$ where appropriate, can be substituted by halogen, —$NO_2$, —$CF_3$, —CN, —OH, —OCH$_3$, —NH$_2$, —NHCOCH$_3$, —OCF$_3$, —CO$_2$—(C$_1$–C$_4$-alkyl), —CO$_2$H, —CONH$_2$, —CONH—(C$_1$–C$_4$-alkyl), —CH$_2$—NHCOCF$_3$, —CH$_2$NH$_2$ and C$_1$–C$_4$-alkyl, R—identical or different radical from the following: C$_1$–C$_4$-alkyl, C$_1$–C$_4$-alkoxy, trifluoromethyl, trichloromethyl, trifluoromethoxy, trichloromethoxy, fluorine, chlorine, bromine, iodine, nitro and cyano, and a fused-on benzene ring which in turn can carry up to two of the radicals mentioned above for R (without the fused-on benzene ring), and n—an integer from 0 to 2, for the fused-on benzene ring 0 or 1.

The invention also relates to the use of compounds I as drugs for human and veterinary medicine.

Derivatives of quinoxaline-2,3(1H,4H)-dione

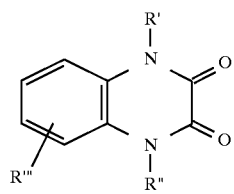

R', R", R'''=substituents have been proposed in several publications for the treatment of disorders of the central nervous system and as hypnotics and sedatives. For example, EP-A315959, EP-A374534 and EP-A377112 describe compounds in which R''' is halogen, nitro, cyano, hydroxyl, trifluoromethyl, C$_1$–C$_4$-alkoxy and the groups —SO$_2$H, SO$_2$R$^x$, —SONH$_2$, —SO$_2$NHR$^x$ and SO$_2$NR$_2^x$, where R$^x$ is C$_1$–C$_4$-alkyl, and a fused-on benzene ring which may also be substituted. In U.S. Pat. No. 3,992,378, the substituent R''' is C$_1$–C$_2$-fluoroalkyl, and in PCT 91/13878, besides halogen and nitro, it is C$_1$–C$_6$-alkyl, alkoxy, aryloxy and aralkoxy.

Furthermore, EP-A 8864 also mentions piperidinyl, pyrrolidinyl and piperazinyl as substituents R'''. Compounds of the latter type are also disclosed in Ind. J. Chem. 28B (1989) 888–890; in an examination, which is also mentioned herein, of their utilizability as helminthicides for controlling hookworms and tapeworms, these compounds proved to be unsuitable.

Imidazolyl- and triazolylquinoxalines have been claimed in WO92/07847, specifically likewise as inhibitors of glutamate receptors.

The known compounds have the disadvantage that they are able to overcome the blood-brain barrier only poorly, if at all, and therefore their effect on the central nervous system is unsatisfactory.

It is an object of the present invention to provide novel and more effective quinoxaline-2,3(1H,4H)-diones.

We have found that this object is achieved by the compounds I defined at the outset.

We have also found various processes, which are described in detail hereinafter, for preparing the quinoxaline-2,3(1H,4H)-diones I and their use as drugs for human and veterinary medicine.

In principle, the compounds I according to the invention can be prepared in a plurality of ways including reaction of an amino-1,2-phenylenediamine II

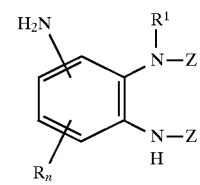

where Z is an acyl protective group, with a succinaldehyde derivative or its acyclic or cyclic acetal or hemiacetal (III) to give IV

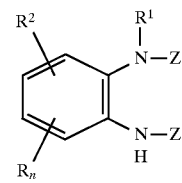

and, after elimination of the protective group Z, carrying out the ring closure to I in a conventional manner with oxalic acid or one of its functional derivatives, or by initially converting II in the form without protective groups with oxalic acid or one of its functional derivatives into the corresponding aminoquinoxaline-2,3(1H, 4H)-diones and then reacting the latter with III to give pyrrolylquinoxaline which is then derivatized in a suitable way to give I.

The compounds I according to the invention can be obtained in the following specific ways:

An amino-1,2-phenylenediamine II where Z is an acyl protective group, preferably acetyl or trifluoroacetyl, is reacted in a conventional way, eg. as described by A. R. Katritzky and C. W. Rees, "Comprehensive Heterocyclic Chemistry", Vol. 4, Part 3.06, pages 313 et seq., in the presence of catalytic amounts of an acid such as acetic acid, with a compound III, preferably the cyclic acetal, with elimination of water to give IV.

The acid can also act as solvent if it is used in larger amounts. However, in general, it is customary to carry out the reaction in a solvent such as toluene or in a mixed solvent such as toluene/dimethylformamide with acid catalysis at from 50° to 150° C., preferably 100° to 150° C., or in concentrated acetic acid at from 50° C. to the boiling point.

After elimination of the protective group, the ring closure to IV is carried out in a conventional way with oxalic acid or one of its functional derivatives, preferably a diester such as dimethyl oxalate or diethyl oxalate, to give I. The temperature and time for the ring closure are generally known. It is likewise possible to prepare with ethyl oxalyl chloride a monoamide which cyclizes to the quinoxaline dione at elevated temperature.

Amino-1,2-phenylenediamines II are disclosed, for example, in U.S. Pat. No. 3,992,378 or can be obtained as described therein. They can furthermore be prepared from commercial o-phenylenediamines after introduction of protective groups in a conventional way by nitration and subsequent reduction of the nitro group.

Another possibility for preparing the starting compound II comprises the generally known reaction of 2-nitrochlorobenzenes with amines such as ethylamine, cyclohexylamine, 1-phenylethylamine and α-aminoacetic acids to give the corresponding 2-nitroanilines, subsequent reduction of the nitro group, introduction of protective groups, and nitration and reduction of the other nitro group.

The reaction of 2-nitrochlorobenzenes with amines is generally known and is normally carried out in polar solvents such as dimethylformamide, dimethyl sulfoxide and ethanol in the presence of basic salts such as potassium carbonate at from 25° to 180° C., preferably from 25° to 140° C.

It is likewise possible to react 2,4-difluoronitrobenzene stepwise with 2 different amines, it being possible to react the fluorine atom in position 2 first (cf., for example, D. D. Davey et al., J. Med. Chem. 34 (1991) 2671). The subsequent exchange of the second halogen with $H_2NR^{11}$(with, for example, $R^{11}$=H or benzyl) leads to diamines VI which are subsequently reduced by methods similar to those described below

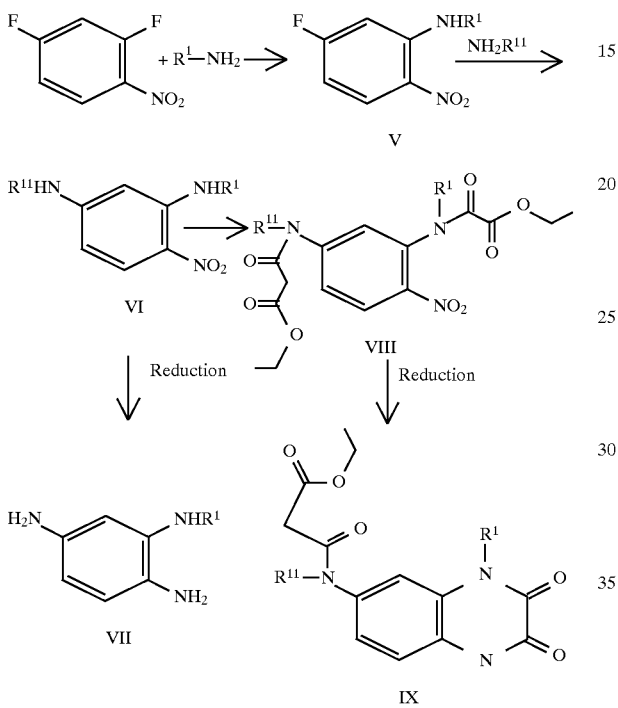

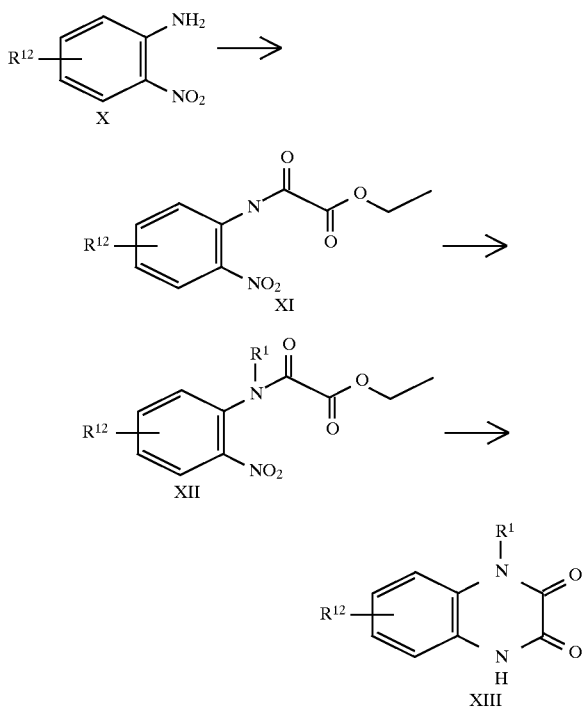

to triamines, which can then be converted into the quinoxalines in a manner corresponding to the compounds IV. The aniline VI can likewise be converted with a monochloride of oxalic acid or appropriately activated oxalic monoesters by known processes (cf. Houben-Weyl, Methoden der org. Chemie, Vol. E5, Chapter V) into the anilides VIII. VIII is converted by reduction, by methods similar to those described below, but especially by reduction with Pd/C and hydrogen, Pd/C and hydrogen donors such as ammonium formate, or with iron and acetic acid, into quinoxalines IX. Subsequent hydrolysis by known processes, such as heating with hydrochloric acid, and catalytic elimination of the benzyl group (if $R^{11}$=benzyl), results in compounds of type II which can be converted as described into the pyrrole derivatives.

Quinoxalines can additionally be obtained from nitroanilines X by preparing the amide XI with oxalic acid derivatives and then converting it by addition of a base such as sodium hydride or potassium tert-butanolate into the amide anion. Addition of a halide results in the amide XII which is converted by reduction, similar to the conversion of VIII into IX, into a quinoxaline XIII which can be derivatized as described below to give the products I. The alkylation is carried out in solvents, preferably polar solvents, such as tetrahydrofuran and dimethylformamide at from 25° to 150° C.

The introduction and elimination of the protective groups takes place in each case by conventional methods which are summarized, for example, in T. W. Greene, "Protective Groups in Organic Synthesis", Wiley and Sons, New York 1982, Chapter 7, pages 249 et seq.

The nitration and reduction steps can in each case be carried out by the usual methods described in Houben-Weyl, "Methoden der organischen Chemie", Vol. 10/1 and Vol. 11/1 respectively. Suitable for the nitration are mixtures of acetic acid and nitric acid or sulfuric acid and sodium nitrate.

The reduction can take place by a chemical or catalytic method. In the catalytic variant, for example reduction is carried out with hydrogen on palladium/active carbon or platinum/active carbon catalysts in the presence of a solvent, it also being possible, however, to use substances such as ammonium formate as hydrogen transfer agents; in the chemical variant it is possible to carry out the reduction with sodium borohydride/copper sulfate in dimethylformamide and in alcohols such as ethanol. Furthermore, it is also customary to reduce the nitro groups with redox systems such as iron/hydrochloric acid and zinc/hydrochloric acid.

Another possibility for preparing the compounds I according to the invention comprises carrying out the steps described above, reaction with III and ring closure, in the reverse sequence.

The ring closure is carried out first by reacting an amino-1,2-phenylenediamine II which is in the form without protective groups with oxalic acid or one of its functional derivatives such as oxalyl chloride or a diester thereof by conventional methods to give the corresponding aminoquinoxaline-2,3(1H,4H)-diones. Before the subsequent reaction with III to give I it is advisable, if further substituents R, for example nitro, are introduced into the aminoquinoxalinedione, to protect the amino group by an acyl group in order then, after elimination of the protective group in the presence of hydrochloric acid, to react either the free aminoquinoxaline-2,3(1H,4H)-diones or their hydrochlorides with III.

The substitution of the pyrrolyl ring claimed in $R^2$ in the products I and IV prepared in this way can be modified in a suitable way. Thus, for example, the aldehyde XIV can be converted by reductive amination with amines $HR^6$ into the compounds I according to the invention. The reductive amination is generally carried out at from 5° to 80° C., preferably 10° to 30° C., in the presence of reducing agents such as sodium cyanoborohydride or hydrogen in the presence of hydrogenation catalysts such as Pd/carbon, Pt/carbon or Raney nickel, expediently in polar organic solvents such as alcohols or dimethylformamide.

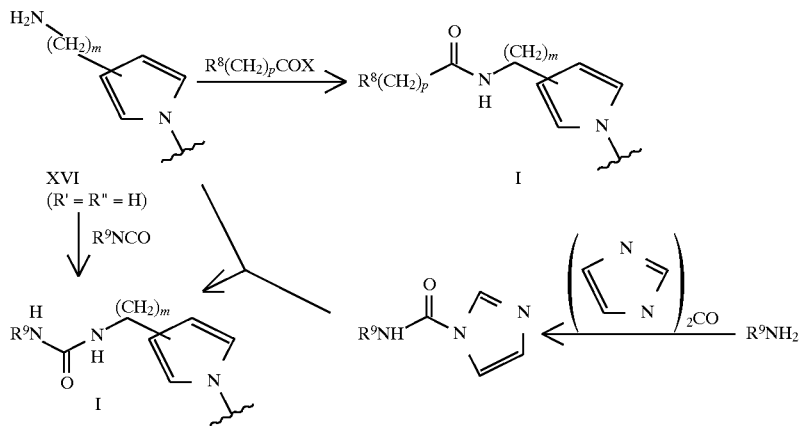

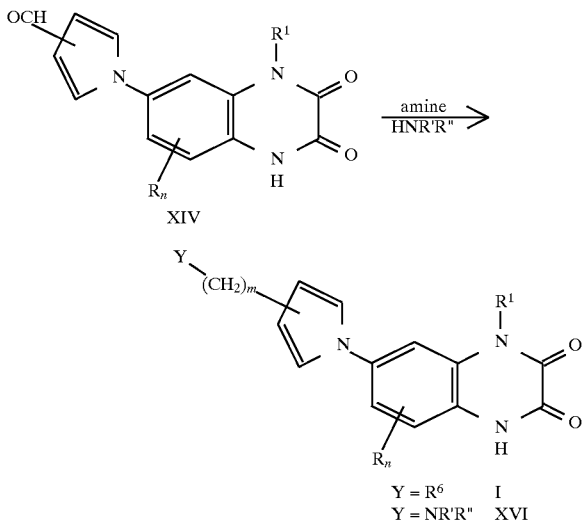

On the other hand, pyrrolylalkylamines XVI obtainable in this way can be converted with acids $R^8(CH_2)_pCO_2H$, which are activated in a suitable way to $R^8(CH_2)_pCOX$ where X is a leaving group such as azide, imidazole and others, which are listed in R. C. Larock, Comprehensive Organic Transformations, New York 1989, pages 972 et seq., into the amides I" according to the invention. This coupling takes place by known processes, which are listed, for example, in Houben-Weyl "Methoden der organischen Chemie", Volume E5, Chapter V.

The pyrrolylalkylamines XVI (R'=R"=H) can likewise be reacted with isocyanates to give the ureas I, and it is also possible to use in place of the isocyanates the amines $HNHR^9$ which are previously reacted in a known manner with phosgene or analogous compounds such as carbonyldiimidazole. These and comparable processes are described, for example, in Houben-Weyl "Methoden der organischen Chemie", Volume E4, pages 334 et seq. These processes are carried out with or without solvent, which would preferably be dimethylformamide, and at from 25° to 150° C.

The compounds I according to the invention are antagonists of the excitatory amino acids, in particular glycine, AMPA and kainate antagonists.

The excitatory amino acids such as glutamic acid are widespread in the central nervous system (CNS). These excitatory amino acids function as transmitter substances for glutamate receptors, of which various subtypes are known. One subtype is, for example, called the NMDA receptor after the specific agonist N-methyl-D-aspartate. This NMDA receptor has various binding sites for agonists or antagonists. The amino acid glycine likewise binds to the NMDA receptor and modulates the action of the natural agonist glutamic acid. Antagonists on this glycine binding site can accordingly show antagonistic effects on the NMDA receptor and inhibit overexcitation of this receptor.

Two other subtypes of the glutamate receptors are the AMPA receptor and the kainate receptor, each of which is named after the specific antagonists, 2-amino-3-hydroxy-5-methyl-4-isoxazolepropionic acid (AMPA) and kainic acid. In a similar manner to the NMDA receptor already mentioned, antagonists of these receptors can likewise inhibit overexcitation.

Elevated glutamate levels occur in a number of neurodegenerative disorders or psychological disturbances and may lead to overexcited states or toxic effects in the CNS.

Antagonists to the glutamate receptor subtypes can thus be used to treat these disorders. Glutamate antagonists, which include, in particular, NMDA antagonists and their modulators (for example glycine antagonists) and the AMPA antagonists, are therefore suitable for therapeutic use for neurodegenerative disorders (Alzheimer's and Parkinson's diseases), neurotoxic disturbances following hypoxia, anoxia or ischemia, as occur after a stroke, or else as antiepileptics, antidepressants and anxiolytics (cf. Arzneim. Forschung 40 (1990) 511–514; TIPS 11 (1990) 334–338 and Drugs of the Future 14 (1989) 1059–1071).

The pharmacological activity of the compounds I according to the invention was investigated on isolated membrane material from rat brains. For this purpose, the membrane material was incubated in the presence of the substances according to the invention with the radiolabeled substances $^3$H-2-amino-3-hydroxy-5-methyl-4-isoxazolepropionic acid ($^3$H-AMPA), $^3$H-5,7-dichlorokynurenic acid or $^3$H-kainate. During this the said radioligands bind in each case to the glutamate receptors specific for them, ie. to AMPA receptors, ($^3$H-5,7-dichlorokynurenic acid-binding) NMDA receptors and kainate receptors respectively. After the incubation, the membranes with the receptor-bound radioligands were separated from the free radioligands, and the radioactivity associated with the membranes as measured by liquid scintillation counting. The concentration of receptor-bound ligands, and the extent of displacement of a given radioligand by particular concentrations of the compounds I according to the invention, can be determined from the radioactivity of the membranes. The dissociation constant $K_I$ (I=inhibitor) resulting therefrom, which is a measure of the displacing action of the agent according to the invention, was determined by iterative non-linear regression analysis using the Statistical Analysis System (SAS) on an IBM computer, similar to the "Ligand" program of P. J. Munson and D. Rodbard (Analytical Biochem. 107 (1980) 220, Ligand: Versatile Computerized Approach for Characterization of Ligand Binding Systems).

The following in vitro investigations were carried out:
1. Binding of $^3$H-2-amino-3-hydroxy-5-methyl-4-isoxazolepropionic acid ($^3$H-AMPA)

To prepare the membrane material, freshly removed rat cerebra were homogenized together with about 15 times the volume of a buffer solution A composed of 30 mM α,α,α-tris(hydroxymethyl)methylamine hydrochloride (TRIS-HCl) and 0.5 mM ethylenediaminetetraacetic (EDTA), pH 7.4, using an Ultra-Turrax. The suspension was centrifuged at 48000 g for 20 minutes. After removal of the supernatant liquid, the protein-containing membrane material present in the sediment was washed three times by suspension in buffer solution A and subsequent centrifugation at 48000 g for 20 minutes each time. The membrane material was then suspended in 15 times the volume of buffer solution A and incubated at 37° C. for 30 minutes. Subsequently, the protein material was washed twice by centrifugation and suspension and stored at −70° C. until used.

For the binding assay, the protein material was thawed at 37° C. and washed twice by centrifugation at 48000 g (20 minutes) and subsequent suspension in buffer solution B composed of 50 mM TRIS-HCl, 0.1M potassium thiocyanate and 2.5 mM calcium chloride, pH 7.1. Subsequently, 0.25 mg of membrane material, 0.1 μCi of $^3$H-AMPA (60 Ci/mmol) and compound I or I' were dissolved in 1 ml of buffer solution B and incubated on ice for 60 minutes. The incubated solution was filtered through a CF/B filter (from Whatman) which had previously been treated with a 0.5% strength aqueous solution of polyethyleneimine for at least 2 hours. Subsequently, the membrane residue was washed with 5 ml of cold buffer solution B in order to separate bound and free $^3$H-AMPA from one another. The radioactivity of the bound $^3$H-AMPA in the membrane material was measured by scintillation counting and then the $K_I$ was determined by evaluation of the displacement plots by regression analysis.

The $K_I$ of N-(1-(6-nitroquinoxaline-2,3(1H,4H)-dion-7-yl)-3-pyrrolyl)methyl)-4-carbamoylpyridinium acetate (Example 3) and 1-carboxymethyl-6-nitro-7-(3-((1-piperidinyl)methyl)-1-pyrrolyl)quinoxaline-2,3(1H,4H)-dione (Example 14) was found to be <10 μM.

2. Binding of $^3$H-5,7-dichlorokynurenic acid

To prepare the membrane material, freshly removed rat cerebra were homogenized together with about 10 times the volume of a buffer solution A' composed of 50 mM TRIS-HCl and 10 mM EDTA, pH 7.4. The suspension was centrifuged at 48000 g for 20 minutes. After removal of the supernatant liquid, the membrane material present in the sediment was washed twice by suspension in buffer solution A' and subsequent centrifugation for 20 minutes each time. After resuspension of the membranes in buffer solution A' and freezing in liquid nitrogen, the suspension was thawed again at 37° C. and, after a further wash, was incubated at 37° C. for 15 minutes. The protein material was subsequently washed four times by centrifugation and suspension and stored at −70° C. until used.

For the binding assay, the protein material was thawed at 37° C. and then washed twice by centrifugation at 48000 g (20 minutes) and subsequent suspension in buffer solution B' composed of 50 mM TRIS-HCl, pH 7.4. Subsequently, 0.15 mg of membrane material, 0.3 μCi of $^3$H-5,7-dichlorokynurenic acid (16 Ci/mmol) and compound I or I' were dissolved in 1 ml of buffer solution B' and incubated on ice for 30 minutes. The incubated solution was centrifuged at 150000 g for 2 minutes. After removal of the supernatant liquid, the sediments were suspended twice in 1.5 ml of cold buffer solution B' each time. After measurement of the radioactivity of the $^3$H-5,7-dichlorokynurenic acid bound to the membranes in the sediment, the $K_I$ was obtained by evaluation of the displacement plots by regression analysis.

The compounds I according to the invention are suitable as drugs for human and veterinary medicine and can be used for the treatment of neurodegenerative disorders and neurotoxic disturbances of the central nervous system and for producing antiepileptics, anxiolytics and antidepressants.

The pharmaceutical compositions according to the invention contain a therapeutically effective amount of the compounds I besides conventional ancillary substances. For local external use, eg. in powders and ointments, the agents are present in a concentration of 0.0001 to 1% by weight, preferably 0.001 to 1% by weight.

For internal use, the preparations are administered in single doses. 0.1–100 mg per kg of body weight are given in a single dose. The compositions can be administered in one or more dosages each day depending on the nature and severity of the disorder.

The pharmaceutical compositions according to the invention contain, besides the agent, the conventional excipients and diluents appropriate for the desired mode of administration. For local external use it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable examples for internal use are lactose, propylene glycol, ethanol, starch, talc and polyvinylpyrrolidone.

It is also possible for antioxidants such as tocopherol and butylated hydroxyanisole as well as butylated hydroxytoluene, flavor-improving additives, stabilizers, emulsifiers and lubricants to be present.

The substances contained in the composition apart from the agent, and the substances used to produce the pharmaceutical composition, are toxicologically acceptable and compatible with the particular agent.

The pharmaceutical compositions are produced in a conventional way, for example by mixing the agent with the other conventional excipients and diluents.

The pharmaceutical compositions can be administered in various ways, such as orally, parenterally, subcutaneously, intraperitoneally and topically. Thus, possible presentations are tablets, emulsions, infusion and injection solutions, pastes, ointments, gels, creams, lotions, powders and sprays.

EXAMPLES

Example 1

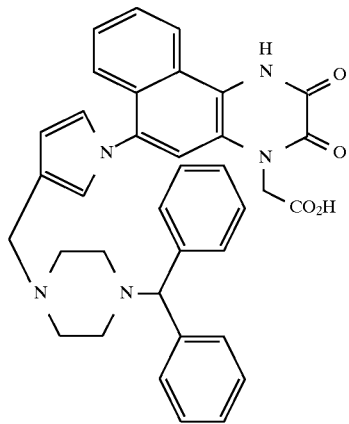

1-Carboxymethyl-9-(3-(4-(1,1-diphenylmethyl)-1-piperazinylmethyl)-1-pyrrolyl)benzo[f]quinoxaline-2,3(1H,4H)-dione a) 2-Methoxy-1-nitronaphthalene 100 g (0.63 mol) of 2-methoxynaphthalene were dissolved in 1.2 l of acetic acid and, at 10° C., 100 ml of 65% strength nitric acid were slowly added dropwise. The mixture was then stirred at 10° C. for 2 h. The resulting precipitate was then filtered off with suction to yield 72.5 g (57%). Melting point 129°–130° C.

$^1$H-NMR (D$_6$-DMSO): δ=4.1 (3H); 7.5–7.8 (4H); 8.05 (1H) and 8.2 (1H) ppm.

b) N-(1-Nitro-2-naphthyl)aminoacetic acid 50 g (0.246 mol) of product 1a, 100 g (1.3 mol) of glycine and 100 g (0.7 mol) of potassium carbonate were heated in 400 ml of diethylene glycol at 140° C. for 10 min. The mixture was then immediately poured into ice-water, acidified with concentrated hydrochloric acid and extracted with 1.5 l of ethyl acetate. The resulting precipitate was filtered off with suction to yield 29.6 g (49%) of the product. Melting point >155° C. (decomposition).

$^1$H-NMR (D$_6$-DMSO): δ=4.3 (2H); 7.2 (1H); 7.35 (1H); 7.6 (1H); 7.8 (1H); 8.0 (1H); 8.4 (1H); 8.7 (1H,NH) and ca. 12 (broad) ppm.

c) N-(1-Amino-2-naphthyl)aminoacetic acid 28 g (0.11 mol) of product 1b were dissolved in 300 ml of ethanol and, after addition of 10 ml of acetic acid and 2 g of palladium/carbon (10%), hydrogenated at room temperature under 1 bar. The mixture was subsequently filtered and the filtrate was concentrated under reduced pressure. 23.9 g (98%) of the product were obtained.

$^1$H-NMR (D$_6$-DMSO): δ=3.8 (2H); 6.2 (NH); 7.1 (1H); 7.2 (1H); 7.3–7.5 (2H); 7.7 (1H); 8.1 (1H) and 10.5 (1H, CO$_2$H) ppm.

d) 1-(Carboxymethyl)benzo[f]quinoxaline-2,3(1H,4H)-dione 22 g (0.1 mol) of product 1c and 28 ml (0.2 mol) of triethylamine were dissolved in 300 ml of anhydrous tetrahydrofuran. Then, at 0°–5° C., 12.5 ml (0.11 mol) of ethyl oxalyl chloride dissolved in 50 ml of anhydrous tetrahydrofuran were added dropwise. The mixture was stirred at 0°–5° C. for 1 h and then concentrated under reduced pressure, and the residue was partitioned between ethyl acetate and water. The organic phase was dried and concentrated under reduced pressure. This residue was refluxed in a mixture of 50 ml of ethanol and 200 ml of concentrated hydrochloric acid for 1.5 h. The mixture was then poured into ice-water and the precipitate was filtered off with suction. 16.8 g (61%) of the product were obtained. Melting point 288°–291° C. (decomposition).

$^1$H-NMR (D$_6$-DMSO): δ=5.0 (2H); 7.4–7.6 (3H); 7.7 (1H); 7.9 (1H); 8.6 (1H); 12.3 (1H) and ca. 13 (broad) ppm.

e) 1-(Ethoxycarbonylmethyl)benzo[f]quinoxaline-2,3(1H,4H)-dione 17 g (62.9 mmol) of product 1d were stirred in a mixture of 250 ml of concentrated sulfuric acid and 70 ml of ethanol at 55° C. for 3 h. The mixture was then poured into ice-water and the precipitate was filtered off with suction. 18.3 g (98%) of the product were obtained. Melting point >250° C.

$^1$H-NMR (D$_6$-DMSO): δ=1.2 (3H); 4.2 (2H); 5.1 (2H); 7.3–7.6 (4H); 7.85 (1H) and 8.7 (1H) ppm.

f) 1-(Ethoxycarbonylmethyl)-9-nitrobenzo[f]quinoxaline-2,3(1H,4H)-dione 18 g (60.3 mmol) of product 1e were suspended in 200 ml of acetic acid and, at room temperature, 50 ml of 65% strength nitric acid were cautiously added. The mixture was then heated to 80° C. After the reaction was complete (color of the solution changed from dark to pale red), the mixture was poured onto ice and the precipitate was filtered off with suction. 16.9 g (82%) of the product were obtained. Melting point >250° C.

$^1$H-NMR (D6-DMSO): δ=1.3 (3H); 4.2 (2H); 5.2 (2H); 7.7 (2H); 8.3–8.4 (2H); 8.8 (1H) and 12.7 (1H) ppm.

g) 9-Amino-1-(ethoxycarbonylmethyl)benzo[f]quinoxaline-2,3(1H,4H)-dione 16.5 g (48 mmol) of product 1f were dissolved in 150 ml of dimethylformamide and, after addition of 1.5 g of palladium/carbon (10%), hydrogenated at room temperature under 1 bar. The mixture was then filtered and the filtrate was concentrated under reduced pressure. 13.1 g (88%) of the product were obtained. Melting point >250° C.

$^1$H-NMR (D$_6$-DMSO): δ=1.2 (3H); 4.2 (2H); 5.0 (2H); 5.7–6.0 (2H, NH, broad); 6.6 (1H); 7.4 (1H); 7.5 (1H); 8.2 (1H); 8.5 (1H) and 12.0 (1H) ppm.

h) 1-Ethoxycarbonylmethyl-9-(3-formyl-1-pyrrolyl)benzo[f]quinoxaline-2,3(1H,4H)-dione 1.8 g (4.6 mmol) of compound 1g and 1.3 g (8 mmol) of 2,5-dimethoxytetrahydrofuran-3-ylcarbaldehyde were refluxed in 100 ml of glacial acetic acid for 15 min. The mixture was then concentrated under reduced pressure and the residue was purified by chromatography on silica gel (mobile phase=toluene/acetone/acetic acid=10/10/1). 2.0 g (65%) of the product were obtained. Melting point 176°–177° C.

$^1$H-NMR (D$_6$-DMSO): δ=1.2 (3H); 4.2 (2H); 5.15 (2H); 6.8 (1H); 7.25 (1H); 7.5–7.8 (3H); 7.9 (1H); 8.0 (1H); 8.75 (1H); 9.8 (1H) and 12.5 (1H) ppm.

i) 1-Carboxymethyl-9-(3-formyl-1-pyrrolyl)benzo[f]quinoxaline-2,3(1H,4H)-dione 1.8 g (4.6 mmol) of compound 1h were suspended in 30 ml of tetrahydrofuran, and 0.4 g (13.8 mmol) of lithium hydroxide dissolved in 40 ml of water was added. The mixture was stirred for 1.5 h and then neutralized with 1M hydrochloric acid, the tetrahydrofuran was removed under reduced pressure, and the precipitate was filtered off with suction. 1.6 g (96%) of the product were obtained.

$^1$H-NMR (D$_6$-DMSO): δ=5.1 (2H); 6.8 (1H); 7.25 (1H); 7.5 (1H); 7.6 (1H); 7.7 (1H); 7.9 (1H); 8.0 (1H); 8.8 (1H); 9.95 (1H) and 12.5 (broad) ppm.

j) 1-Carboxymethyl-9-(3-(4-(1,1-diphenylmethyl)-1-piperazinylmethyl)-1-pyrrolyl)benzo[f]quinoxaline-2,3(1H, 4H)-dione 0.7 g (1.9 mmol) of compound 1i, 1.0 g (3.9 mmol) of 4-(1,1-diphenylmethyl)piperazine and 0.12 mol of glacial acetic acid were suspended in 75 ml of dimethylformamide/ethanol (1:4) and, at room temperature, 0.12 g (1.9 mmol) of sodium cyanoborohydride was added in portions. The mixture was stirred at room temperature for 16 h and then concentrated under reduced pressure and partitioned between methylene chloride and water. The organic phase was dried and concentrated under reduced pressure. The residue was dissolved in a little methanol and precipitated using ether/pentane to yield 0.38 g (34%) of the product. Melting point >250° C.

$^1$H-NMR (D$_6$-DMSO): δ=2.2–2.6 (8H); 3.4 (2H); 4.6 (2H); 6.2 (1H); 6.9 (1H); 6.95 (1H); 7.1–7.6 (14H) and 8.8 (1H) ppm.

Example 2

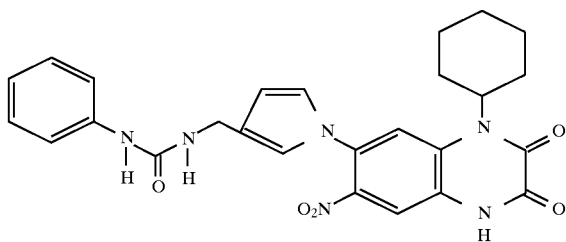

N-(1-(1-Cyclohexyl-6-nitroquinoxaline-2,3(1H,4H)-dion-7-yl)-3-pyrrolyl)methyl-N'-phenylurea a) 4-Chloro-N-cyclohexyl-2-nitroaniline 51.5 g (0.27 mol) of 2,5-dichloronitrobenzene, 22.3 g (0.27 mol) of cyclohexylamine, 74.6 g (0.54 mol) of potassium carbonate and 0.5 g of 18-crown-6 were heated in 300 ml of dimethylformamide at 100° C. for 4 h. The mixture was then poured into water and extracted with ethyl acetate. The organic phase was dried and concentrated under reduced pressure. The residue was recrystallized from i-propanol, resulting in 42.3 g (62%) of the product. Melting point 101°–103° C.

$^1$H-NMR (D$_6$-DMSO): δ=1.2–2.0 (10H); 3.7 (1H); 7.1 (1H); 7.5 (1H); 8.0 (1H) and 8.05 (1H) ppm.

b) 2-Amino-4-chloro-N-cyclohexylaniline 41.6 g (0.16 mol) of 4-chloro-N-cyclohexyl-2-nitroaniline were dissolved in 400 ml of ethanol, 4.2 g of Raney nickel were added, and the mixture was hydrogenated at 25° C. under 1 bar. The mixture was then filtered and the filtrate was concentrated under reduced pressure. 37.3 g (100%) of the product were obtained.

$^1$H-NMR (D$_6$-DMSO): δ=1.2–2.0 (10H); 3.1 (1H); 4.0–5.0 (3H, broad) and 6.3–6.6 (3H) ppm.

c) 6-Chloro-1-cyclohexylquinoxaline-2,3(1H,4H)-dione 34.5 g (0.15 mol) of 2-amino-4-chloro-N-cyclohexylaniline were refluxed in 500 ml of diethyl oxalate for 4 h. After cooling, the precipitate was filtered off with suction, washed with n-pentane and dried. 26.8 g (63%) of the product were obtained. Melting point 265°–266° C.

$^1$H-NMR (D$_6$-DMSO): δ=1.1–1.9 (8H); 2.3–2.5 (2H); 4.4 (1H); 7.1 (2H); 7.6 (1H) and 12 (broad) ppm.

d) 6-Chloro-1-cyclohexyl-7-nitroquinoxaline-2,3(1H,4H)-dione 26.3 g (94 mmol) of 6-chloro-1-cyclohexylquinoxaline-2,3(1H,4H)-dione were dissolved in 275 ml of concentrated sulfuric acid and subsequently, at 0° C., 9.5 g (94 mmol) of potassium nitrate were added in portions. The mixture was then stirred at 0° C. for 30 min and at 25° C. for 2 h and subsequently poured into ice-water, and the precipitate was filtered off with suction. 29.5 g (97%) of the product were obtained. Melting point >300° C.

$^1$H-NMR (D$_6$-DMSO): δ=1.1–1.9 (8H); 2.3–2.5 (2H); 4.4 (1H); 7.3 (1H) and ca. 12.5 (1H) ppm.

e) 7-Amino-6-chloro-1-cyclohexylquinoxaline-2,3(1H,4H)-dione (e1) and 7-amino-1-cyclohexylquinoxaline-2,3(1H,4H)-dione (e2)

28.9 g (89 mmol) of 6-chloro-1-cyclohexyl-7-nitroquinoxaline-2,3(1H,4H)-dione were dissolved in 300 ml of tetrahydrofuran/methanol/dimethylformamide (3:3:1) and, after addition of 3 g of palladium/carbon (10%), hydrogenated. The mixture was filtered, the carbon was washed with methanolic ammonia solution, and the combined filtrates were concentrated under reduced pressure. The residue was chromatographed on silica gel with the mobile phase toluene/acetone/glacial acetic acid (10:10:1). 2.2 g (8%) of product e1 and 18.5 g (80%) of product e2 were obtained.

e1:
$^1$H-NMR (D$_6$-DMSO): δ=1.1–2.0 (8H); 2.3–2.5 (2H); 4.4 (1H); ca. 5.2 (2H, broad); 7.0 (1H); 7.1 (1H) and ca. 11.5 (broad) ppm.

e2:
$^1$H-NMR (D$_6$-DMSO): δ=1.1–2.0 (8H); 2.3–2.5 (2H); 4.4 (1H); ca. 5.1 (2H, broad); 6.4 (1H); 6.8 (1H); 6.9 (1H) and ca. 11.5 (broad) ppm.

f) 7-Acetamido-1-cyclohexylquinoxaline-2,3(1H,4H)-dione 18.3 g (70 mmol) of 7-amino-1-cyclohexylquinoxaline-2,3(1H,4H)-dione (product e2 from Example 2) were dissolved in 250 ml of acetic acid and, after a spatula tip of 4-(N,N-dimethylamino)pyridine had been added, 7.2 g (70 mmol) of acetic anhydride were added dropwise. The mixture was then stirred at room temperature for 30 min. The resulting precipitate was then filtered off with suction and dried to yield 20.8 g (98%) of the product. Melting point 227°–230° C. (decomposition).

$^1$H-NMR (D$_6$-DMSO): δ=1.1–1.9 (8H); 2.3–2.5 (2H); 4.5 (1H); 7.1 (1H); 7.3 (1H); 8.0 (1H); 10.0 (1H) and ca. 12.0 (broad) ppm.

g) 7-Amino-1-cyclohexyl-6-nitroquinoxaline-2,3(1H,4H)-dione 20.6 g (68 mmol) of 7-acetamido-1-cyclohexylquinoxaline-2,3(1H,4H)-dione were dissolved in 250 ml of concentrated sulfuric acid. Then, at 0°–5° C., 7.2 g (71 mmol) of potassium nitrate were added in portions. The mixture was then stirred at 0° C. for 30 min and at room temperature for 2 h. The mixture was subsequently poured into 1.5 l of ice-water and heated on a waterbath for 4 h. The resulting precipitate was filtered off with suction. The filtrate was adjusted to pH 6 with a little ammonia solution and extracted with methylene chloride. The organic phase was dried and concentrated under reduced pressure. This residue and the first precipitate were combined. 13.4 g (64%) of the product were obtained. Melting point >260° C.

$^1$H-NMR (D6-DMSO): δ=1.1–2.0 (8H); 2.3–2.5 (2H); 4.3 (1H); 7.1 (1H); 7.1–7.4 (broad, 2H); 7.7 (1H) and ca. 11.5 (1H) ppm.

h) 1-Cyclohexyl-6-nitro-7-(3-trifluoroacetamidomethyl-1-pyrrolyl)-quinoxaline-2,3(1H,4H)-dione 8 g (26 mmol) of compound 2g and 8.45 g (33 mmol) of compound 4a were heated in 200 ml of glacial acetic acid at 60° C. for 1 h. The mixture was then poured into ice-water and the precipitate was filtered off with suction. 11.7 g (93%) of the product were obtained. Melting point 247°–248° C.

$^1$H-NMR (D$_6$-DMSO): δ=1.0–3.0 (10H); 4.2–4.7 (3H); 6.75 (1H); 7.0–7.1 (2H); 7.7 (1H); 7.9 (1H); 9.9 (1H) and ca. 12.5 (1H) ppm.

i) 7-(3-Aminomethyl-1-pyrrolyl)-1-cyclohexyl-6-nitroquinoxaline-2,3(1H,4H)-dione 11.1 g (23 mmol) of compound 2h were suspended in 250 ml of ethanol, and 50 ml of 2M sodium hydroxide solution were added. The mixture was stirred at room temperature for 10 minutes and then neutralized with 2M hydrochloric acid, the solution was buffered with aqueous sodium bicarbonate solution and the resulting precipitate was filtered off with suction. 7.9 g (90%) of the product were obtained. Melting point >300° C.

$^1$H-NMR (CD$_3$OD, NaOH): δ=1.2–2.2 (10H); 3.3 (1H); 3.8 (2H); 6.25 (1H); 6.3 (1H) and 6.6–6.8 (3H) ppm.

j) N-(1-(1-Cyclohexyl-6-nitroquinoxaline-2,3(1H,4H)-dion-7-yl)-3-pyrrolyl)methyl-N'-phenylurea 1.5 g (4 mmol) of product 2 i and 0.04 g (4 mmol) of triethylamine were added to 25 ml of anhydrous dimethylformamide, and 0.52 g (4.4 mmol) of phenyl isocyanate were added. The mixture was then stirred at 70° C. for 1 h and subsequently poured into ice-water and extracted with ethyl acetate. The organic phase was dried and concentrated under reduced pressure. The residue was treated with hot isopropanol and filtered off with suction. 1.5 g (74%) of the product were obtained. Melting point 172° C. (decomposition).

$^1$H-NMR (D$_6$-DMSO): δ=1.1–1.9 (8H); 2.4 (2H); 4.15 (2H); 4.4 (1H); 6.25 (1H); 6.3 (1H), 6.9 (3H); 7.2 (2H); 7.4 (2H); 7.6 (1H); 7.8 (1H); 8.5 (1H) and 12.5 (broad) ppm.

Example 3

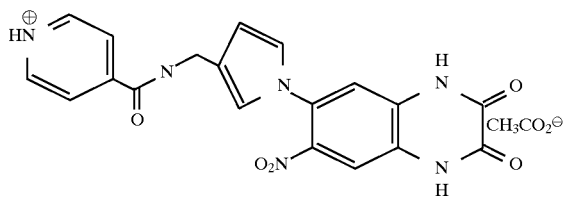

N-((1-(6-Nitroquinoxaline-2,3(1H,4H)-dion-7-yl)-3-pyrrolyl)methyl)-4-carbamoylpyridinium acetate a) Preparation of 6-trifluoroacetamidoquinoxaline-2,3(1H,4H)-dione A solution of 28 g (0.16 mol) of 6-aminoquinoxaline-2,3(1H,4H)-dione in 200 ml of trifluoroacetic acid was refluxed with 35.7 g (0.17 mol) of trifluoroacetic anhydride for one hour. The mixture was cooled and then the precipitated crude product was filtered off with suction and worked up by conventional methods. Yield: 83%. Melting point >330° C.

$^1$H-NMR (D$_6$-DMSO): δ=7.1 (1H); 7.3 (1H); 7.6 (1H); 11.3 (1H); 12.1 (1H) ppm.

b) Preparation of 6-trifluoroacetamido-7-nitroquinoxaline-2,3-(1H,4H)-dione

A solution of 39 g (0.14 mol) of 6-trifluoroacetamidoquinoxaline -2,3(1H,4H)-dione in 500 ml of concentrated sulfuric acid was cooled to 0° C., 12.1 g (0.14 mol) of sodium nitrate were added in portions, and the mixture was stirred at room temperature for 30 minutes. It was subsequently poured into ice-water and the crude product was filtered off and worked up by conventional methods. Yield: 95%. Melting point >320° C.

$^1$H-NMR (D$_6$-DMSO): δ=7.3 (1H); 7.8 (1H); 11.6 (1H); 12.2 (1H); 12.4 (1H) ppm.

c) Preparation of 6-amino-7-nitroquinoxaline-2,3(1H,4H)-dione

A solution of 41 g (0.13 mol) of 6-trifluoroacetamido-7-nitroquinoxaline -2,3(1H,4H)-dione in 300 ml of ethanol and 700 ml of 3 molar hydrochloric acid was refluxed for 3 hours. After the mixture had cooled, the precipitated crude product was filtered off with suction and washed with acetone. Yield: 84%. Melting point >330° C.

$^1$H-NMR (D$_6$-DMSO): δ=6.6 (1H), 7.2–7.6 (3H); 7.8 (1H); 11.7 (1H); 12.1 (1H) ppm.

d) Preparation of N-(2,5-dimethoxy-3-tetrahydrofuranyl)methyl)isonicotinamide 3.8 g (31.0 mmol) of isonicotinic acid and 5.5 g (34.1 mmol) of 3-aminomethyl-2,5-dimethoxytetrahydrofuran (DE-A 2,645,234) were dissolved in 100 ml of anhydrous dimethylformamide. At 0° C., a solution of 7.3 ml (34.1 mmol) of diphenylphosphoryl azide in 30 ml of anhydrous dimethylformamide and, after 15 minutes, 8.5 ml (68.24 mmol) of triethylamine were added. The mixture was stirred for 16 h and then concentrated under reduced pressure, the residue was partitioned between ethyl acetate and aqueous sodium bicarbonate solution, and the organic phase was separated off, dried and concentrated under reduced pressure. 5.5 g of an impure product were obtained and were immediately reacted further.

e) N-((1-(6-Nitroquinoxaline-2,3(1H,4H)-dion-7-yl)-3-pyrrolyl)methyl-4-carbamoylpyridinium acetate 150 ml of acetic acid were heated to about 100° C. and then successively 1.5 g (6.8 mmol) of product 3c and 1.8 g (6.8 mmol) of product 3d were added. The mixture was stirred at 100° C. for 30 minutes and then allowed to cool. The precipitate was filtered off with suction, suspended in acetone and again filtered off with suction. 2.2 g (70%) of the product were obtained. Melting point 182°–185° C. (decomposition).

$^1$H-NMR (D$_6$-DMSO): δ=1.9 (3H); 4.4 (2H); 6.25 (1H); 6.85 (2H); 7.1 (1H); 7.8 (3H); 8.7 (2H); 9.15 (1H); 11.9 (broad, 1H); 12.1 (1H) and 12.3 (1H) ppm.

Example 4

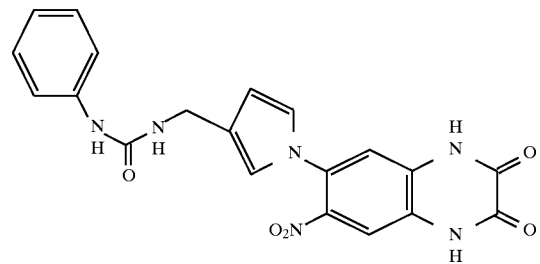

N-(1-(6-Nitroquinoxaline-2,3(1H,4H)-dion-7-yl)-3-pyrrolylmethyl)-N'-phenylurea a) Preparation of N-((2,5-dimethoxy-3-tetrahydrofuranyl)methyl)trifluoroacetamide 50 g (0.31 mol) of 3-aminomethyl-2,5-dimethoxytetrahydrofuran, 31.7 g (0.31 mol) of triethylamine and a little 4-(N,N-dimethylamino)pyridine were dissolved in 300 ml of anhydrous ether and, at 0° to 5° C., 65.1 g (0.31 mol) of trifluoroacetic anhydride dissolved in 100 ml of anhydrous ether were added dropwise. The mixture was then stirred for 1 h and subsequently washed with water, dried and concentrated under reduced pressure. 70.5 g of the abovementioned product, which was impure and was reacted further without further purification, were obtained.

b) Preparation of 6-nitro-7-(3-(trifluoroacetamidomethyl)-1-pyrrolyl)quinoxaline-2,3(1H,4H)-dione 4 g (18 mmol) of compound 3c and 6 g (23.3 mmol) of crude product 4a were added successively to 150 ml of glacial acetic acid which had been heated to 100° C. The mixture was stirred for about 15 to 30 minutes and, after cooling, the acetic acid was removed under reduced pressure, and the residue was suspended in ether and filtered off with suction. 6.0 g (85%) of the product were obtained. Melting point >220° C. (decomposition).

$^1$H-NMR (D$_6$-DMSO): δ=4.25 (2H); 6.2 (1H); 6.8 (2H); 7.1 (1H); 7.8 (1H); 9.8 (1H) and ca. 12.5 (2H) ppm.

c) Preparation of 7-(3-aminomethyl-1-pyrrolyl)-6-nitroquinoxaline-2,3(1H,4H)-dione 20 g (50.4 mmol) of compound 4b were suspended in 300 ml of tetrahydrofuran, and 5.4 g (22.4 mmol) of lithium hydroxide dissolved in 150 ml of water were added. The mixture was stirred at room temperature for 3 h. The tetrahydrofuran was then removed under reduced pressure, and the remaining aqueous phase was acidified with dilute hydrochloric acid and then buffered with aqueous sodium bicarbonate solution. The resulting precipitate was filtered off with suction, suspended in acetone and again filtered off with suction. 10 g (66%) of the product were obtained. Melting point >300° C.

$^1$H-NMR (D6-DMSO):
δ=3–4 (NH); 3.8 (2H); 6.25 (1H); 6.9–7.0 (3H); 7.75 (1H) and ca. 11.3 (broad) ppm.

d) N-(1-(6-Nitroquinoxaline-2,3(1H,4H)-dion-7-yl)-3-pyrrolylmethyl)trifluoroacetamide 1.5 g (5 mmol) of compound 4c, 0.7 g (5.9 mmol) of phenyl isocyanate and a spatula tip of 4-(N,N-dimethylamino)pyridine were heated at 110°–120° C. in 100 ml of anhydrous dimethylformamide until the precipitate had dissolved. The mixture was then poured into ice-water, aqueous sodium bicarbonate solution was added, and the resulting precipitate was filtered off with suction and then suspended in ethyl acetate and filtered off with suction twice. 1.3 g (62%) of the product were obtained. Melting point >300° C.

$^1$H-NMR (D$_6$-DMSO): δ=4.15 (2H); 6.1 (1H); 6.7–6.9 (5H); 7.2 (2H); 7.4 (1H); 7.65 (1H) and 8.9 (1H) ppm.

Example 5

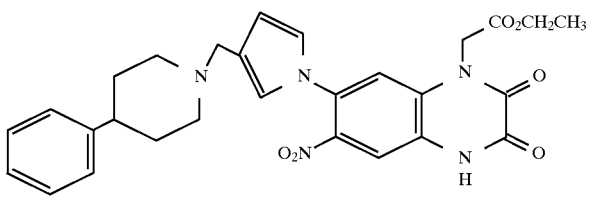

1-(Ethoxycarbonylmethyl)-6-nitro-7-(3-((4-phenyl-1-piperidinyl)methyl)-1-pyrrolyl)quinoxaline-2,3(1H,4H)-dione a) N-(4-Chloro-2-nitrophenyl)glycine 26.2 g (0.137 mol) of 2,5-dichloro-1-nitrobenzene, 20.6 g (0.274 mol) of glycine and 18.9 g (0.137 mol) of potassium carbonate were heated in 200 ml of diethylene glycol at 120° C. for 1 h. After cooling, 100 ml of water were added and the solution was acidified with 1M hydrochloric acid. The precipitate was filtered off with suction. 17.1 g (54%) of the product were obtained.

$^1$H-NMR (D$_6$-DMSO): δ=4.2 (2H); 6.9 (1H); 7.5 (1H); 8.1 (1H); 8.4 (1H) and ca. 13 (broad) ppm.

b) Ethyl N-(4-chloro-2-nitrophenyl)aminoacetate 87.1 g (0.38 mol) of N-(4-chloro-2-nitrophenyl)glycine were suspended in 500 ml of 10% strength ethanolic sulfuric acid and heated to 80° C. The resulting clear solution was poured into 1.5 l of ice-water and the solution was then neutralized with concentrated ammonia solution and sodium bicarbonate solution. The precipitate was filtered off with suction. 84.4 g (89%) of the product were obtained.

$^1$H-NMR (D$_6$-DMSO): δ=1.2 (3H); 4.2 (2H); 4.3 (2H); 7.0 (1H); 7.5 (1H); 8.0 (1H) and 8.4 (1H) ppm.

c) Ethyl N-(4-chloro-2-nitrophenyl)-N-(ethoxycarbonylmethyl)oxamate 86.1 g (0.33 mol) of compound 5b were dissolved in 350 ml of pyridine and, at room temperature, 67.6 g (0.495 mol) of ethyl oxalyl chloride were added dropwise. The mixture was stirred at room temperature for 16 h and then poured into ice-water and acidified with 4M hydrochloric acid. The precipitate was filtered off to afford 120 g of impure product.

$^1$H-NMR (D$_6$-DMSO): δ=1.1–1.3 (6H); 4.0 (2H); 4.2 (2H); 4.5 (1H); 4.6 (1H); 7.7 (1H); 8.0 (1H) and 8.3 (1H) ppm.

d) 6-Chloro-1-(ethoxycarbonylmethyl)quinoxaline-2,3(1H,4H)-dione 101.3 g (0.28 mol) of ethyl N-(4-chloro-2-nitrophenyl)-N-(ethoxycarbonylmethyl) oxamate were dissolved in 1 l of acetic acid and heated to 80° C. Then 15.8 g (0.28 mol) of iron powder was added in portions. After 2 h, a further 15.8 g (0.28 mol) of iron powder were added. Half an hour later the mixture was poured into ice-water and acidified with 4M hydrochloric acid. The precipitate was filtered off with suction to afford 75.7 g (95%) of the product.

$^1$H-NMR (D$_6$-DMSO): δ=1.2 (3H); 4.2 (2H); 5.0 (2H); 7.2 (2H); 7.3 (1H) and 12.3 (1H) ppm.

e) 6-Chloro-1-(ethoxycarbonylmethyl)-7-nitroquinoxaline-2,3(1H,4H)-dione 69.8 g (0.25 mol) of 6-chloro-1-(ethoxycarbonylmethyl)quinoxaline-2,3(1H,4H)-dione were dissolved in 625 ml of concentrated sulfuric acid and, at 0° C., 25 g (0.25 mol) of potassium nitrate were added in portions. The cooling was then removed and the mixture was stirred further. After reaction was complete, the mixture was poured into ice-water and the precipitate was filtered off with suction. 77.8 g (95%) of the product were obtained.

$^1$H-NMR (D$_6$-DMSO): δ=1.3 (3H); 4.2 (2H); 5.0 (2H); 7.3 (1H); 8.2 (1H) and 12.5 (1H) ppm.

f) 7-Amino-1-(ethoxycarbonylmethyl)quinoxaline-2,3(1H, 4H)-dione 84.3 g (0.26 mol) of 6-chloro-1-(ethoxycarbonylmethyl)-7-nitroquinoxaline-2,3(1H,4H)-dione were suspended in 1.5 l of isopropanol and successively 194.2 g (3.1 mol) of ammonium formate dissolved in 500 ml of water, and 8.5 g of palladium/carbon (10%) were added. The mixture was then heated at 75° C. for 4 h and, after cooling, filtered, and the filter cake was extracted three times with 800 ml of dimethylformamide. The combined dimethylformamide phases were concentrated under reduced pressure, and the residue was washed with water. 53.2 g (79%) of the product were obtained.

$^1$H-NMR (D$_6$-DMSO): δ=1.2 (3H); 4.2 (2H); 4.8 (2H); 5.2 (broad, 2H); 6.4 (1H); 6.5 (1H); 6.9 (1H) and 12 (1H) ppm.

g) 7-Acetamido-1-(ethoxycarbonylmethyl)quinoxaline-2,3(1H,4H)-dione 52.95 g (0.2 mol) of 7-amino-1-(ethoxycarbonylmethyl)quinoxaline-2,3(1H,4H)-dione and a spatula tip of 4-(N,N-dimethyl-amino)pyridine were suspended in a mixture of 500 ml of glacial acetic acid and 300 ml of tetrahydrofuran and heated to 50° C. Then 20.5 g (0.2 mol) of acetic anhydride were added dropwise, and the mixture was heated at 50° C. for 2 h. The precipitate was filtered off with suction. 57.8 g (94%) of the product were obtained.

$^1$H-NMR (D6-DMSO): δ=1.2 (3H); 2.05 (3H); 4.2 (2H); 4.9 (2H); 7.1 (1H); 7.3 (1H); 7.55 (1H); 10.0 (1H) and 12 (1H) ppm.

h) 7-Amino-1-(carboxymethyl)-6-nitroquinoxaline-2,3(1H, 4H)-dione 57.5 g (0.19 mol) of 7-acetamido-1-(ethoxycarbonylmethyl)quinoxaline-2,3(1H,4H)-dione were dissolved in 575 ml of concentrated sulfuric acid. The solution was cooled to 0° C., and 19.0 g (0.19 mol) of potassium nitrate were added in portions. The cooling was then removed, and the mixture was stirred. After reaction was complete, the mixture was poured into 2 l of ice-water and heated on a waterbath for 2 h. The pH was then adjusted to about 4–5 with aqueous ammonia solution, and the precipitate was filtered off with suction. The filtrate was concentrated under reduced pressure, and the residue was purified by chromatography on silica gel (mobile phase: methanol:tetrahydrofuran:water=5:4:1+2.5% glacial acetic acid). The resulting product was combined with the first precipitate to afford 36.9 g (70%) of product.

$^1$H-NMR (D$_6$-DMSO): δ=4.5 (2H); 6.7 (1H); 7.3 (2H) and 7.7 (1H) ppm.

i) 7-Amino-1-(ethoxycarbonylmethyl)-6-nitroquinoxaline-2,3(1H,4H)-dione 30.7 g (0.11 mol) of 7-amino-1-(carboxymethyl)-6-nitroquinoxaline-2,3(1H,4H)-dione were suspended in 500 ml of 10% strength ethanolic sulfuric acid and refluxed for 2 h. The mixture was then poured into ice-water, and the resulting precipitate was filtered off with suction. 29.3 g (87%) of the product were obtained.

$^1$H-NMR (D$_6$-DMSO): δ=1.2 (3H); 4.2 (2H); 4.8 (2H); 6.7 (1H); 7.0–7.6 (broad, 2H); 7.8 (1H) and 12.0 (1H) ppm.

j) 1-(Ethoxycarbonylmethyl)-7-(3-formyl-1-pyrrolyl)-6-nitroquinoxaline-2,3(1H,4H)-dione 5.0 g (1.6 mmol) of the product from Example 5i and 2.9 g (1.8 mmol) of 2,5-dimethoxytetrahydrofuran-3-ylcarbaldehyde were introduced into 100 ml of acetic acid at 80°–90° C. The mixture was stirred for 30 minutes and then poured into ice-water, and the precipitate was filtered off with suction. 5.3 g (86%) of the product were obtained.

$^1$H-NMR (D$_6$-DMSO): δ=1.2 (3H); 4.15 (3H); 4.15 (2H); 5.05 (2H); 6.7 (1H); 7.15 (H); 7.8 (1H); 8.0 (1H); 9.8 (1H) and 12,3 (broad) ppm.

k) 1-(Ethoxycarbonylmethyl)-6-nitro-7-(3-((4-phenyl-1-piperidinyl)methyl)-1-pyrrolyl)quinoxaline-2,3(1H,4H)-dione 1.5 g (3.9 mmol) of compound 5j, 1.3 g (7.8 mmol) of 4-phenylpiperidine and 0.5 ml (7.8 mmol) of acetic acid were added to 150 ml of dimethylformamide/ethanol (1:2). At room temperature, 0.24 g (3.9 mmol) of sodium cyanoborohydride was added in portions, and the mixture was stirred for 16 h and then concentrated under reduced pressure. The residue was partitioned between methylene chloride and aqueous sodium bicarbonate solution, and the organic phase was dried and concentrated under reduced pressure. 1.1 g (55%) of the product were obtained.

$^1$H-NMR (D$_6$-DMSO): δ=1.2 (3H), 1.5–1.9 (5H); 1.9–2.2 (2H); 3.0 (2H); 3.4 (2H); 4.1 (1H); 5.1 (2H); 6.25 (1H); 6.85 (1H); 6.9 (1H); 7.1–7.5 (5H); 7.6 (1H); 7.8 (1H) and ca. 12 (broad) ppm.

Example 6

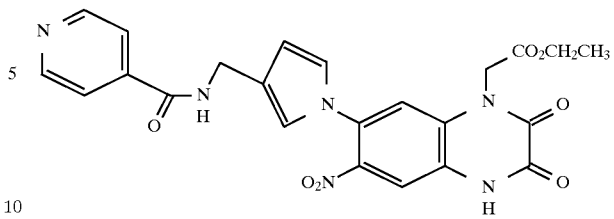

1-(Ethoxycarbonylmethyl)-6-nitro-7-(3-(4-pyridylamido)methyl-1-pyrrolyl)quinoxaline-2,3(1H,4H)-dione 1.1 g (3.6 mmol) of compound 5i and 1.9 g (7.2 mmol) of the crude product 3d were refluxed in 80 ml of glacial acetic acid for 30 minutes. The mixture was then concentrated under reduced pressure and the residue was recrystallized from ethanol. 1.2 g (69%) of the product were obtained. Melting point 165°–167° C. (decomposition).

$^1$H-NMR (D$_6$-DMSO): δ=1.2 (3H); 4.1 (2H); 4.4 (2H); 5.1 (2H); 6.3 (1H); 6.9 (2H); 7.55 (1H); 7.8 (2H); 7.85 (1H); 8.7 (2H); 9.1 (1H) and 12.5 (broad) ppm.

Example 7

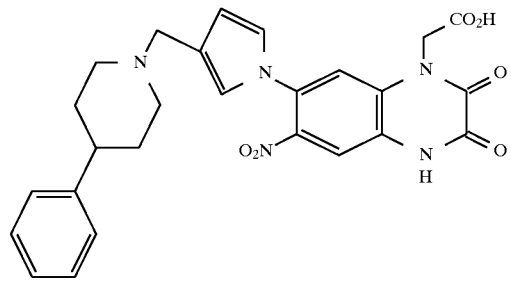

1-Carboxymethyl-6-nitro-7-(3-((4-phenyl-1-piperidinyl)methyl)-1-pyrrolyl)quinoxaline-2,3(1H,4H)-dione 1.0 g (1.9 mmol) of Example 5 was suspended in 10 ml of tetrahydrofuran, and 0.14 g (5.6 mmol) of lithium hydroxide dissolved in 15 ml of water was added. The mixture was stirred at room temperature for 1 h and then the tetrahydrofuran was removed under reduced pressure, and the product was precipitated by cautious addition of 1M hydrochloric acid. 0.8 g (95%) was obtained. Melting point >210° C.

$^1$H-NMR (as NH$_4^+$ salt) (D$_6$-DMSO): δ=1.6–1.8 (4H); 2.0 (2H); 2.4–2.6 (1H); 3.0 (2H); 3.4 (2H); 4.5 (2H); 6.2 (1H); 6.75 (1H); 6.8 (1H); 6.95 (1H); 7.1–7.4 (5H) and 7.7 (1H) ppm.

Example 8

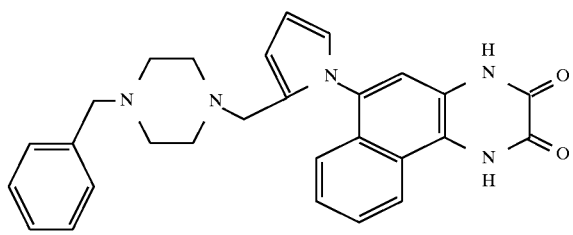

9-(2-(4-Benzyl-1-piperazinyl)methyl-1-pyrrolyl)benzo[f]quinoxaline-2,3(1H,4H)-dione a) 9-(2-Formyl-1-pyrrolyl)benzo[f]quinoxaline-2,3(1H,4H)-dione 7.0 g (30.8 mmol) of 9-aminobenzo[f]quinoxaline-2,3(1H,4H)-dione and 6.4 g (30.8 mmol) of 2,5-dimethoxy-2-(1,1-dimethoxymethyl)tetrahydrofuran were refluxed in 170 ml of glacial acetic acid for 30 minutes. The precipitate was filtered off with suction and purified by chromatography on silica gel (mobile phase: toluene/acetone/glacial acetic acid= 10/10/1). 2.5 g (27%) of the product were obtained. Melting point >250° C.

$^1$H-NMR (D$_6$-DMSO): δ=6.6 (1H); 7.0 (1H); 7.3–7.4 (2H); 7.45 (2H); 7.6 (1H); 8.65 (1H); 9.4 (1H) and ca. 12.3 (broad) ppm.

b) 9-(2-(4-Benzyl-1-piperazinyl)methyl-1-pyrrolyl)benzo[f]-quinoxaline-2,3(1H,4H)-dione 1.1 g (3.6 mmol) of compound 8a, 1.3 g (7.2 mmol) of N-benzylpiperazine and 0.45 ml (7.2 mmol) of glacial acetic acid were added to 150 ml of dimethylformamide/ethanol (1/2) and, at room temperature, 0.23 g (3.6 mmol) of sodium cyanoborohydride was added in portions. The mixture was stirred for 16 h and then concentrated under reduced pressure. The residue was treated with boiling ethanol and filtered off with suction. 0.8 g (51%) of the product was obtained. Melting point >250° C.

$^1$H-NMR (D$_6$-DMSO): δ=1.9–2.3 (8H); 3.0 (1H); 3.25 (1H); ca. 3.4 (2H); 6.2 (2H); 6.9 (1H); 7.05 (1H); 7.2–7.35 (5H); 7.35 (1H); 7.45 (1H); 7.6 (1H); 8.65 (1H) and 12.3 (broad) ppm.

Example 9

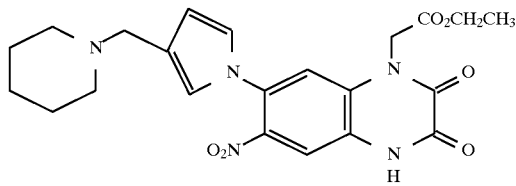

1-Ethoxycarbonylmethyl-6-nitro-7-(3-(1-piperidinyl)methyl-1-pyrrolyl)quinoxaline-2,3(1H,4H)-dione 2.0 g (52 mmol) of compound 5j and 0.9 g (10.4 mmol) of piperidine were reacted by method 5k. 1.6 g (69%) of the product were obtained. Melting point >130° C. (decomposition).

$^1$H-NMR (D$_6$-DMSO): δ=1.2 (3H); 1.4–1.6 (6H); 2.3–2.5 (4H); 3.4 (2H); 4.2 (2H); 5.1 (2H); 6.2 (1H); 6.8 (1H); 6.9 (1H); 7.5 (1H) and 7.85 (1H) ppm.

Example 10

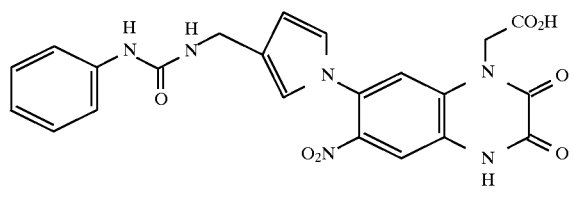

N-(1-(1-Carboxymethyl-6-nitroquinoxaline-2,3(1H,4H)-dion-7-yl)-3-pyrrolyl)methyl-N'-phenylurea a) 1-Ethoxycarbonylmethyl-6-nitro-7-(3-(trifluoroamidomethyl)-1-pyrrolyl)-quinoxaline-2,3(1H,4H)-dione 1.5 g (4.9 mmol) of compound 5i and 2.5 g (9.7 mmol) of compound 4a were added successively to 100 ml of glacial acetic acid which had been heated to 100° C. The mixture was then stirred for about 10 minutes and subsequently poured into ice-water, and the aqueous phase was extracted with ethyl acetate. The organic phase was washed with aqueous sodium bicarbonate solution, dried and concentrated under reduced pressure. The residue was suspended in ethanol and filtered off with suction. 1.7 g (73%) of the product were obtained. Melting point 223° C.

$^1$H-NMR (D$_6$-DMSO): δ=1.2 (3H); 4.15 (2H); 4.3 (2H); 5.05 (2H); 6.2 (1H); 6.9 (2H); 7.55 (1H); 7.9 (1H); 9.8 (1H) and 12.5 (broad) ppm b) 7-(3-(Aminomethyl)-1-pyrrolyl)-1-carboxymethyl-6-nitroquinoxaline-2,3(1H,4H)-dione 0.9 g (1.9 mmol) of compound 10a were dissolved in 20 ml of tetrahydrofuran, and 0.18 g (7.5 mmol) of lithium hydroxide dissolved in 25 ml of water was added. The mixture was stirred at room temperature for 2 h and then neutralized with 1M hydrochloric acid. The precipitate was filtered off with suction, suspended in methanol and again filtered off with suction. 0.55 g (100%) of the product was obtained. Melting point >270° C.

$^1$H-NMR (as K$^+$ salt) (D$_2$O): δ=4.0 (2H); 4.8 (2H); 6.4 (1H); 6.9 (1H); 7.0 (1H); 7.1 (1H) and 7.9 (1H) ppm.

c) N-(1-(1-Carboxymethyl-6-nitroquinoxaline-2,3(1H,4H)-dion-7-yl)-3-pyrrolyl)methyl-N'-phenylurea 1.2 g (3.3 mmol) of compound 10b, 1 ml (6.7 mmol) of triethylamine and 0.44 g (3.7 mmol) of phenyl isocyanate were heated in 40 ml of anhydrous dimethylformamide at 125° C. for 30 minutes. The mixture was then concentrated under reduced pressure, and the residue was partitioned between ethyl acetate and dilute hydrochloric acid. The organic phase was separated off, dried and concentrated under reduced pressure. The residue was recrystallized from i-propanol to afford 0.9 g (57%) of the product. Melting point >210° C. (decomposition).

$^1$H-NMR (D$_6$-DMSO): δ=4.15 (2H); 5.0 (2H); 6.25 (1H); 6.3 (1H, NH); 6.9 (3H); 7.2 (2H); 7.4 (2H); 7.5 (1H); 7.9 (1H); 8.4 (1H, NH) and 12.5 (broad) ppm.

Example 11

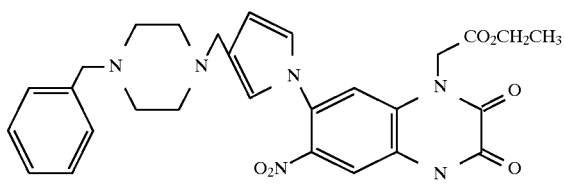

7-(3-((4-Benzyl-1-piperazinyl)methyl)-1-pyrrolyl)-1-ethoxycarbonylmethyl-6-nitroquinoxaline-2,3(1H,4H)-dione 1.9 g (4.9 mmol) of compound 5j and 1.7 g (9.8 mmol) of 4-benzylpiperazine were reacted as in method 5k. 1.3 g (49%) of the product were obtained.

$^1$H-NMR (D$_6$-DMSO): δ=1.2 (3H); 2.3–2.6 (8H); 3.5 (2H); 4.15 (2H); 5.1 (2H); 6.2 (1H); 6.8 (1H); 6.9 (1H); 7.2–7.4 (5H); 7.6 (1H) and 7.9 (1H) ppm.

Example 12

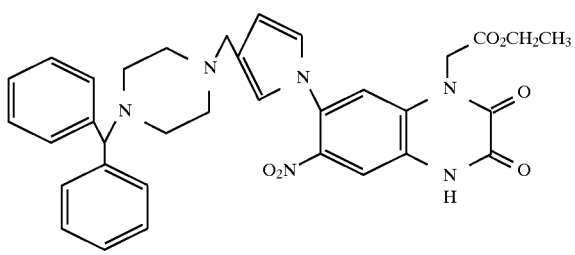

7-(3-((4-(1,1-Diphenylmethyl)-1-piperazinyl)methyl)-1-pyrrolyl)-1-ethoxycarbonylmethyl-6-nitroquinoxaline-2,3(1H,4H)-dione 2.0 g (5.2 mmol) of compound 5j and 2.6 g of 4-(diphenylmethyl)piperazine were reacted as in method 5k. 1.9 g (60%) of the product were obtained.

$^1$H-NMR (D$_6$-DMSO): δ=1.2 (3H); 2.2–2.5 (8H); ca. 3.3 (2H); 4.1 (2H); 4.25 (1H); 5.05 (2H); 6.2 (1H); 6.7 (1H); 6.8 (1H); 7.1–7.5 (11H) and 7.75 (1H) ppm.

Example 13

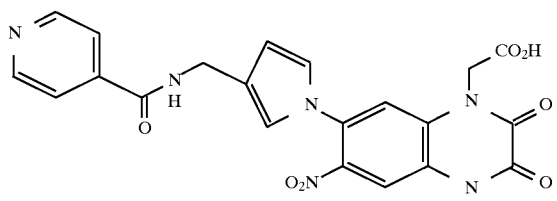

1-(Carboxymethyl)-6-nitro-7-(3-(4-pyridylamido)methyl-1-pyrrolyl)quinoxaline-2,3(1H,4H)-dione 1.2 g (2.4 mmol) of Example 6 were suspended in 30 ml of tetrahydrofuran, and 0.17 g (7.3 mmol) [lacuna] dissolved in 30 ml of water was added. The mixture was stirred at room temperature for 1 h and then the tetrahydrofuran was removed under reduced pressure, the aqueous phase was neutralized with 1M hydrochloric acid, and the precipitate was filtered off with suction. 1.0 g (91%) of the product was obtained. Melting point 250° C.

$^1$H-NMR (K$^+$ salt in D$_2$O): δ=4.4 (2H); 4.7 (2H); 6.3 (1H); 6.8 (2H); 7.0 (1H); 7.6 (2H); 7.8 (1H) and 8.6 (2H) ppm.

Example 14

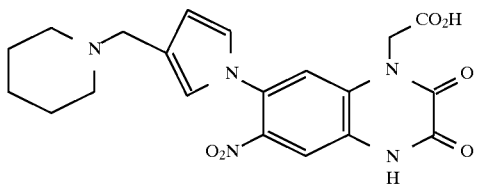

1-Carboxymethyl-6-nitro-7-(3-((1-piperidinyl)methyl)-1-pyrrolyl)quinoxaline-2,3(1H,4H)-dione 1.2 g (2.6 mmol) of Example 9 and 0.2 g (7.9 mmol) of lithium hydroxide were reacted as in Example 7. 0.9 g (81%) of the product was obtained. Melting point >250° C.

$^1$H-NMR (K$^+$salt in D$_2$O): δ=1.4–1.9 (6H); 2.7–3.0 (4H); 3.8 (2H); 4.4 (2H); 6.4 (1H); 6.9 (1H); 7.0 (1H); 7.1 (1H) and 7.9 (1H) ppm.

Example 15

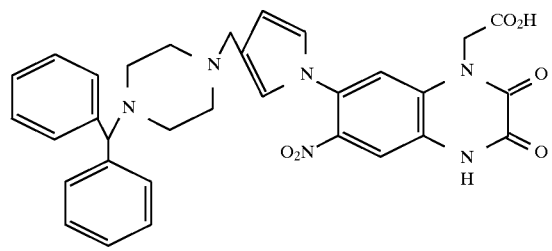

1-Carboxymethyl-7-(3-(4-(1,1-diphenylmethyl)-1-piperazinyl)methyl-1-pyrrolyl)-6-nitroquinoxaline-2,3(1H,4H)-dione 1.5 g (2.4 mmol) of Example 12 and 0.17 g (7.2 mmol) of lithium hydroxide were reacted as in Example 7. 1.2 g (84%) of the product were obtained. Melting point >245° C.

$^1$H-NMR (D$_6$-DMSO): δ=2.2–2.5 (4H); 3.3–3.7 (6H); 4.25 (1H); 4.6 (2H); 6.1 (1H); 6.8 (2H); 7.1–7.5 (11H) and 7.8 (1H) ppm.

Example 16

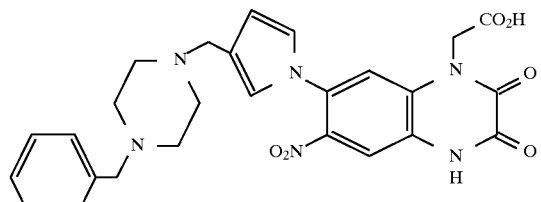

7-(3-((4-Benzyl-1-piperazinyl)methyl)-1-pyrrolyl)-1-carboxymethyl-6-nitroquinoxaline-2,3(1H,4H)-dione 1.3 g (3.4 mmol) of product 5j and 1.2 g (6.7 mmol) of N-benzylpiperazine were reacted as in Example 1j. 1.4 g (80%) of the product were obtained. Melting point >230° C.

¹H-NMR (DMSO, KOH): δ=2.2–2.5 (4H); 3.3–3.6 (8H); 4.4 (2H); 6.1 (1H); 6.65 (1H); 6.7 (1H); 6.8 (1H); 7.2–7.4 (5H) and 7.5 (1H) ppm.

Example 17

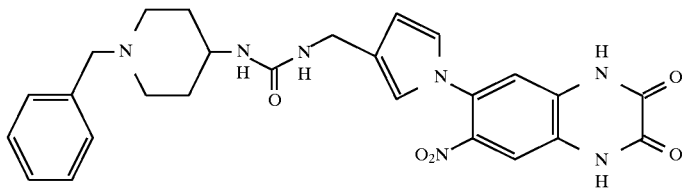

N-(1-Benzyl-4-piperidinyl)-N'-(1-(6-nitroquinoxaline-2,3(1H,4H)-dion-7-yl)-3-pyrrolyl)methylurea 1.5 g (5 mmol) of compound 4c, 1.3 g (8 mmol) of carbonyldiimidazole and 1.5 g (8 mmol) of 4-amino-1-benzylpiperidine were reacted in dimethylformamide as in Example 18. The resulting precipitate was twice suspended in ethanol and filtered off with suction. 1.2 g (46%) of the product were obtained. Melting point 234°–237° C.

¹H-NMR (D₆-DMSO): δ=1.3 (2H); 1.7 (2H); 2.0 (2H); 2.7 (2H); 3.4 (3H); 4.05 (2H); 5.8 (1H); 5.9 (1H); 6.2 (1H); 6.75 (1H); 6.8 (1H); 7.05 (1H); 7.2–7.4 (5H) and 7.8 (1H) ppm.

Example 18

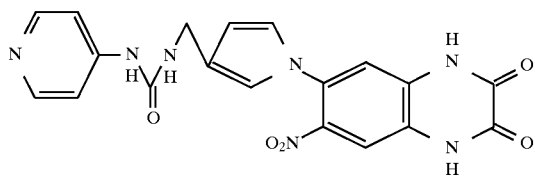

N-(1-(6-Nitroquinoxaline-2,3(1H,4H)-dion-7-yl)-3-pyrrolyl)methyl-N'-(4-pyridyl)urea 0.7 g (7.4 mmol) of 4-aminopyridine and a spatula tip of 4-(N,N-dimethylamino)pyridine were dissolved under protective gas in 100 ml of anhydrous dimethylformamide and, at room temperature, 1.3 g (8 mmol) of carbonyldiimidazole were added. The mixture was stirred at room temperature for 60 minutes and then at 50° C. for 30 minutes. Subsequently 1.5 g (5 mmol) of compound 4c were added, and the mixture was heated to 80°–90° C., whereupon the precipitate slowly dissolved. The reaction solution was poured into ice-water, aqueous sodium bicarbonate was added, and the resulting precipitate was filtered off with suction and then suspended in tetrahydrofuran/acetone and again filtered off with suction. 1.5 g (71%) of the product were obtained. Melting point 238°–242° C. (decomposition).

¹H-NMR (D₆-DMSO): δ=4.2 (2H); 6.2 (1H); 6.8 (2H); 7.0 (1H); 7.4 (1H); 7.75 (1H); 8.25 (1H); 8.4 (1H); 9.1 (1H) and 10.1 (broad) ppm.

Example 19

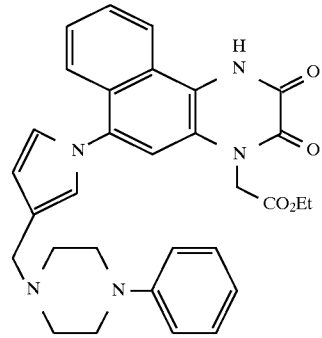

1-Ethoxycarbonylmethyl-9-(3-(4-phenyl-1-piperazinyl)methyl-1-pyrrolyl)benzo[f]-quinoxaline-2,3(1H,4H)-dione 2.0 g (5.1 mmol) of product 1h and 1.7 g (10.2 mmol) of N-phenylpiperazine were reacted as in method 1j. 1.5 g (59%) of the product were obtained. Melting point >140° C. (decomposition).

¹H-NMR (D₆-DMSO): δ=1.2 (3H); 2.6 (4H); 3.2 (5H); 3.5 (1H); 4.2 (2H); 5.1 (2H); 6.3 (1H); 6.8 (1H); 6.9–7.0 (4H); 7.1–7.3 (2H); 7.4–7.8 (4H); 8.7–8.8 (1H) and ca. 12.3 (broad) ppm.

Example 20

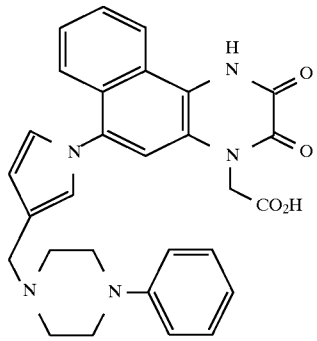

1-Carboxymethyl-9-(3-(4-phenyl-1-piperazinyl)methyl-1-pyrrolyl)benzo[f]quinoxaline-2,3(1H,4H)-dione 1.3 g (2.4 mmol) of Example 19 and 0.12 g (4.9 mmol) of lithium hydroxide were reacted as in Example 7. 0.9 g (76%)

of the product was obtained. Melting point >250° C. (decomposition).

$^1$H-NMR (CD$_3$COOD): δ=3.3 (4H); 3.8 (4H); 4.4 (2H); 5.2 (2H); 6.55 (1H); 6.95 (1H); 7.0–7.2 (3H); 7.3 (3H); 7.6 (2H); 7.8 (2H) and 8.5 (1H) ppm.

Example 21

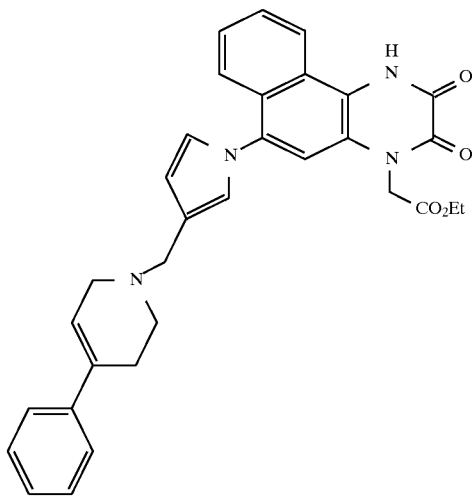

1-Ethoxycarbonylmethyl-9-(3-(4-phenyl-1,2,5,6-tetrahydro-1-pyridinyl)methyl-1-pyrrolyl)benzo[f]quinoxaline-2,3(1H,4H)-dione 2 g (5.1 mmol) of product 1h and 2 g (10.2 mmol) of 4-phenyl-1,2,5,6-tetrahydropyridine were reacted as in Example 1j. 1.4 g (53%) of the product were obtained. Melting point >150° C. (decomposition).

$^1$H-NMR (D$_6$-DMSO): δ=1.2 (3H); 2.55 (2H); 2.8 (2H); 3.2 (2H); 3.6 (2H); 4.2 (2H); 5.2 (2H); 6.2 (1H); 6.3 (1H); 7.05 (2H); 7.2–7.5 (5H); 7.6 (2H); 7.7 (2H); 8.8 (1H) and ca. 12 (broad) ppm.

Example 22

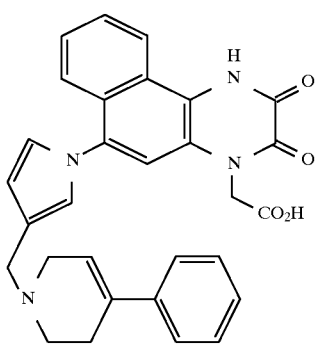

1-Carboxymethyl-9-(3-(4-phenyl-1,2,5,6-tetrahydro-1-pyridinyl)methyl-1-pyrrolyl)benzo[f]quinoxaline-2,3(1H,4H)-dione 1.2 g (2.3 mmol) of Example 21 and 0.11 g (4.6 mmol) of lithium hydroxide were reacted as in Example 7. 0.9 g (79%) of the product was obtained. Melting point >250° C.

$^1$H-NMR (CD$_3$COOD): δ=2.8 (1H); 3.0 (1H); 3.35 (1H); 3.8–4.0 (2H); 4.2 (1H); 4.45 (2H); 5.2 (2H); 6.1 (1H); 6.5 (1H); 7.1 (1H); 7.2–7.4 (4H); 7.45 (2H); 7.6 (2H); 7.75 (2H) and 8.45 (1H) ppm.

Example 23

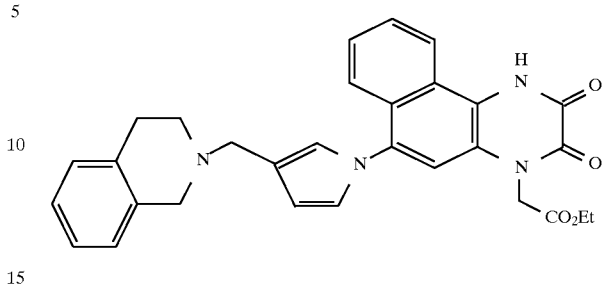

1-Ethoxycarbonylmethyl-9-(3-(1,2,3,4-tetrahydro-2-isoquinolinyl)methyl-1-pyrrolyl)benzo[f]quinoxaline-2,3(1H,4H)-dione 2.0 g (5.1 mmol) of product 1h and 1.4 g (10.2 mmol) of 1,2,3,4-tetrahydroisoquinoline were reacted as in method 1j. 1.8 g (70%.) of the product were obtained. Melting point >140° C. (decomposition).

$^1$H-NMR (D$_6$-DMSO): δ=1.2 (3H); 2.6–3.0 (4H); 3.6 (3H); 4.0–4.3 (3H); 5.15 (2H); 6.3 (1H); 6.9–7.2 (6H); 7.4–7.8 (4H); 7.75 (1H) and ca. 11.8 (broad) ppm.

Example 24

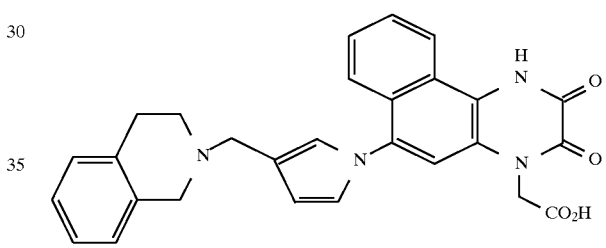

1-Carboxymethyl-9-(3-(1,2,3,4-tetrahydro-2-isoquinolinyl)methyl-1-pyrrolyl)benzo[f]quinoxaline-2,3(1H,4H)-dione 1.6 g (3.2 mmol) of Example 23 and 0.15 g (6.3 mmol) of lithium hydroxide were reacted as in Example 7. 1.3 g (87%) of the product were obtained. Melting point >250° C.

$^1$H-NMR (CD$_3$COOD): δ=3.1 (1H); 3.3–3.5 (2H); 4.0 (1H); 4.35 (1H); 4.5 (2H); 4.7 (1H); 5.2 (2H); 6.6 (1H); 7.1 (1H); 7.15–7.4 (5H); 7.6 (2H); 7.8 (2H) and 8.5 (1H) ppm.

Example 25

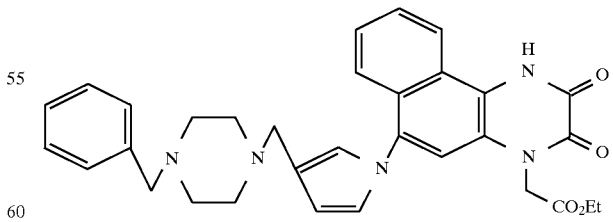

9-(3-(4-Benzyl-1-piperazinyl)methyl-1-pyrrolyl)-1-ethoxycarbonylmethylbenzo[f]quinoxaline-2,3(1H,4H)-dione 6.0 g (15.3 mmol) of product 1h and 5.4 g (30.7 mmol) of 4-benzylpiperazine were reacted as in method 1j. 4.5 g (54%) of the product were obtained. Melting point >220° C. (decomposition)

$^1$H-NMR as dihydrochloride (D$_6$-DMSO): δ=1.2 (3H); 3.2–3.8 (10H); 4.15 (2H); 4.3 (2H); 5.2 (2H); 6.6 (1H); 7.15 (1H); 7.3 (1H); 7.4–7.8 (9H); 8.75 (1H) and 12.5 (1H) ppm.

Example 26

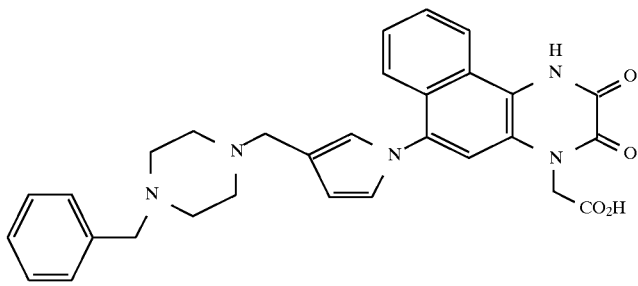

9-(3-(4-Benzyl-1-piperazinyl)methyl-1-pyrrolyl)-1-carboxymethylbenzo[f]quinoxaline-2,3(1H,4H)-dione 4.5 g (8.2 mmol) of Example 25 and 0.4 g (16.3 mmol) of lithium hydroxide were reacted as in Example 7. 3.5 g (84%) of the product were obtained. Melting point >230° C.

$^1$H-NMR as potassium salt (D$_6$-DMSO): δ=2.3–2.5 (4H); 3.2–3.6 (8H); 4.5 (2H); 6.2 (1H); 6.9 (1H); 6.95 (1H); 7.2–7.6 (9H) and 7.85 (1H) ppm.

Example 27

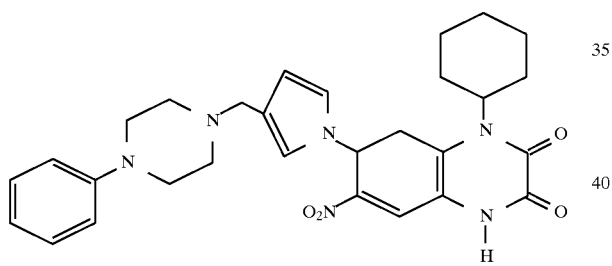

a) 1-Cyclohexyl-6-(3-formyl-1-pyrrolyl)-7-nitroquinoxaline-2,3(1H,4H)-dione 4 g (13 mmol) of product 2g, 2.3 g (14 mmol) of 2,5-dimethoxytetrahydrofuran-3-ylcarbaldehyde and a spatula tip of 4-toluenesulfonic acid were refluxed in 200 ml of dimethylformamide/toluene (1:1) with a water trap. After reaction was complete (TLC check), the mixture was concentrated under reduced pressure and the residue was partitioned between ethyl acetate and water. The organic phase was dried and concentrated under reduced pressure. This residue was purified by chromatography on silica gel (mobile phase: toluene/acetone/glacial acetic acid=40/20/1). 1.1 g (22%) of the product were obtained. Melting point 176° C. (decomposition).

$^1$H-NMR (D$_6$-DMSO): δ=1.1–2.5 (10H); 4.5 (1H); 6.7 (1H); 7.2 (1H); 7.25 (1H); 8.3 (1H); 9.8 (1H) and 12.5 (1H) ppm.

b) 1-Cyclohexyl-6-nitro-7-(3-(4-phenyl-1-piperazinyl)methyl-1-pyrrolyl)quinoxaline-2,3(1H (1H,4H)-dione 2.0 g (5.2 mmol) of product 28a and 1.7 g (10.5 mmol) of N-phenylpiperazine were reacted as for compound 1j, 2.3 g (84%) of the product were obtained. Melting point 185° C. (decomposition).

Example 28

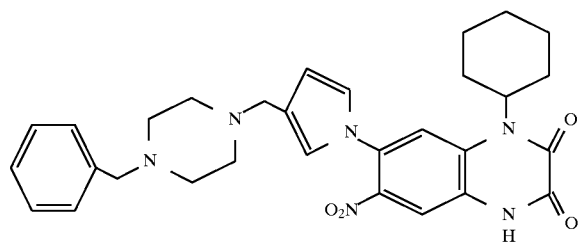

7-(3-(4-Benzyl-1-piperazinyl)methyl-1-pyrrolyl)-1-cyclohexyl-6-nitroquinoxaline-2,3(1H,4H)-dione 2.0 g (5.2 mmol) of product 27a and 1.8 g (10.5 mmol) of N-benzylpiperazine were reacted as for product 1j. 2.1 g (73%) of the product were obtained. Melting point 185° C. (decomposition).

Example 29

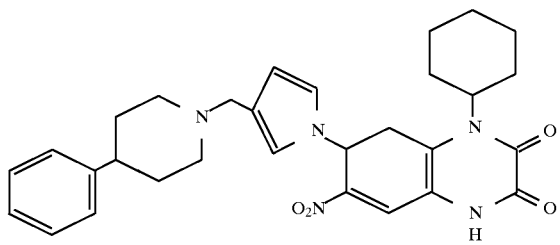

1-Cyclohexyl-6-nitro-7-(3-(4-phenyl-1-piperidinyl)methyl-1-pyrrolyl)quinoxaline-2,3(1H,4H)-dione 2.0 g (5.2 mmol) of product 27a and 1.7 g (10.5 mmol) of 4-phenylpiperidine were reacted as for product 1j. 2.4 g (86%) of the product were obtained. Melting point >200° C. (decomposition).

Example 30

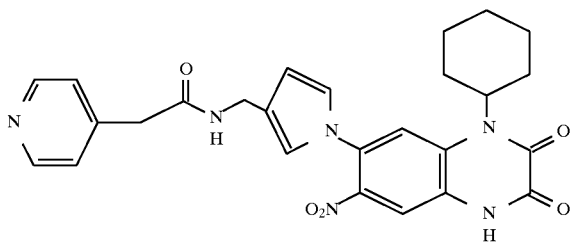

1-Cyclohexyl-6-nitro-7-(3-((4-pyridylmethyl)amido)methyl-1-pyrrolyl)quinoxaline-2,3(1H,4H)-dione 1.8 g (13.4 mmol) of 4-pyridylacetic acid were dissolved in 100 ml of anhydrous dimethylformamide, and 2.4 g (14.7 mmol) of carbonyldiimidazole were added. The mixture was stirred at room temperature for 30 minutes and then at 50° C. for a further 30 minutes. Then 4.3 g (11.3 mmol) of product 2i were added and the mixture was stirred at 80° C. for 1 h. It was subsequently poured into ice-water and the resulting aqueous phase was adjusted to pH 9 with sodium bicarbonate. The precipitate was filtered off with suction. 4.8 g (86%) of the product were obtained. Melting point >200° C.

$^1$H-NMR (D$_6$-DMSO): δ=1.1–1.9 (8H); 2.2–2.4 (2H); 3.5 (2H); 4.1 (2H); 4.4 (1H); 6.1 (1H); 6.7–7.0 (2H); 7.2 (2H); 7.5 (1H); 7.8 (1H) and 8.4 (3H) ppm.

Example 31

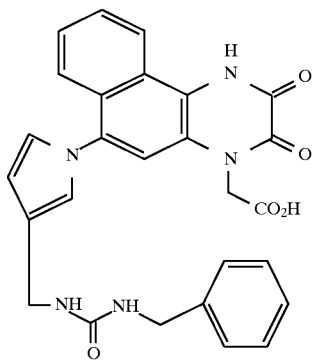

N-(1-(1-carboxymethylbenzo[f]quinoxaline-2,3(1H,4H)-dion-9-yl)-3-pyrrolyl)methyl-N'-phenylurea a) 1-Ethoxycarbonylmethyl-9-(3-(trifluoromethylamidomethyl)-1-pyrrolyl)benzo[f]quinoxaline-2,3(1H,4H)-dione 5.0 g (16 mmol) of 9-amino-1-ethoxycarbonylmethylbenzo[f]quinoxaline-2,3(1H,4H)-dione (compound 1g) and 4.1 g (16 mmol) of compound 3d were boiled in 170 ml of glacial acetic acid for 20 minutes. After cooling, the precipitate was filtered off with suction. 6.2 g (80%) of the product were obtained. Melting point 246°–247° C.

$^1$H-NMR (D$_6$-DMSO): δ=1.2 (3H); 4.2 (2H); 4.3 (2H); 5.2 (2H); 6.3 (1H); 7.0 (2H); 7.5–7.8 (4H); 8.7 (1H); 9.8 (1H) and 12.5 (1H) ppm.

b) 9-(3-Aminomethyl-1-pyrrolyl)-1-carboxymethylbenzo[f]-quinoxaline-2,3(1H,4H)-dione 160 ml of tetrahydrofuran were added to 6.0 g (12.3 mmol) of product 31a, and 0.88 g (36.9 mmol) of lithium hydroxide dissolved in 100 ml of water was added. The mixture was stirred at room temperature for 90 minutes and then the tetrahydrofuran was removed under reduced pressure and the resulting aqueous phase was acidified with 1M hydrochloric acid. The resulting precipitate was filtered off with suction. 4.0 g (90%) of the product were obtained.

$^1$H-NMR (CD$_3$COOD, D$_2$O): δ=4.3 (2H); 5.2 (2H); 6.55 (1H); 7.1 (1H); 7.25 (1H); 7.5 (1H); 7.6–8.0 (3H) and 8.5 (1H) ppm.

c) N-(1-(1-carboxymethylbenzo[f]quinoxaline-2,3(1H,4H)-dion-9-yl)-3-pyrrolyl)methyl-N'-phenylurea 0.9 g (2.5 mmol) of product 31b and 0.3 g (2.6 mmol) of phenyl isocyanate were stirred in 20 ml of anhydrous dimethylformamide at 120° C. for 30 minutes. The mixture was then concentrated under reduced pressure, and the residue was crystallized from ethanol. 1.1 g (93%) of the product were obtained. Melting point >230° C.

$^1$H-NMR (D$_6$-DMSO): δ=4.2 (2H); 5.0 (2H); 6.3 (2H); 6.9 (1H); 7.0 (2H); 7.15 (2H); 7.35 (2H); 7.5–7.8 (4H); 8.4 (1H); 8.7 (1H) and 12.5 (1H) ppm.

Example 32

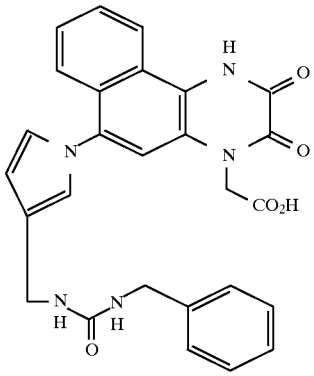

N'-Benzyl-N-(1-(1-carboxymethylbenzo[f]quinoxaline-2,3(1H,4H)-dion-9-yl)-3-pyrrolyl)methylurea 0.9 g (2.5 mmol) of product 31b and 0.37 g (2.7 mmol) of benzyl isocyanate were heated in 30 ml of dimethylformamide at 120° C. for 20 minutes. The mixture was then concentrated under reduced pressure, and the residue was crystallized using ethanol. 1.1 g (92%) of the product were obtained. Melting point >210° C. (decomposition).

$^1$H-NMR (D$_6$-DMSO): δ=4.1–4.3 (4H); 5.1 (2H); 6.2 (1H); 6.3 (1H); 6.35 (1H); 6.95 (1H); 7.0 (1H); 7.1–7.3 (5H); 7.6 (3H); 7.7 (1H); 8.7 (1H); 12.5 (1H) and ca. 13.5 (broad) ppm.

Example 33

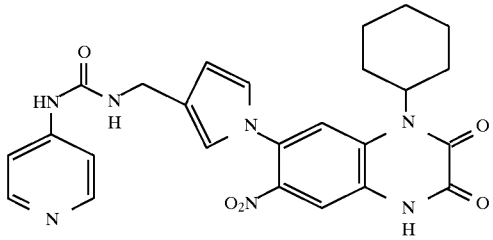

N-(1-(1-Cyclohexyl-6-nitroquinoxaline-2,3(1H,4H)-dion-7-yl)-3-pyrrolyl)methyl-N'-(4-pyridyl)urea 2.0 g (5.2 mmol) of product 2i and 0.5 g (5.2 mmol) of 4-aminopyridine were reacted as in Example 18. 1.4 g (52%) of the product were obtained. Melting point >200° C.

$^1$H-NMR (CD$_3$COOD): δ=1.3 (1H); 1.45 (2H); 1.7 (1H); 1.8–2.0 (4H); 2.5–2.7 (2H); 4.5 (3H); 6.4 (1H); 6.8 (1H); 6.9 (1H); 7.4 (1H); 7.65 (1H); 7.85 (1H); 7.90 (1H) and 9.1 (1H) ppm.

Example 34

N-(1-(1-Cyclohexyl-6-nitroquinoxaline-2,3(1H,4H)-dion-7-yl)-2-pyrrolyl)methyl-N'-phenylurea

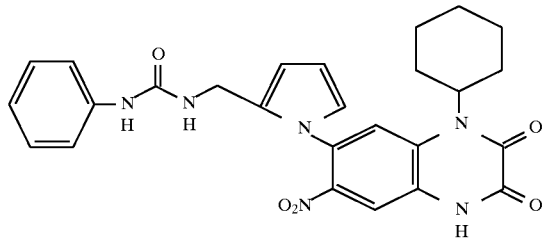

a) (N-((2,5-Dimethoxy-2-tetrahydrofuranyl)methyl) trifluoroacetamide 25.0 g (155 mmol) of 2-aminomethyl-2,5-dimethoxytetrahydrofuran, 15.7 g (155 mmol) of triethylamine and 1 spatula tip of 4-(N,N-dimethylamino)pyridine were dissolved in 200 ml of ether. At 0°–50° C., 32.6 g (155 mmol) of trifluoroacetic anhydride were added dropwise. The mixture was stirred for 1 h and then the ether phase was washed with water, dried and concentrated under reduced pressure. 32 g (80%) of a crude product were obtained and were used further.

b) 1-Cyclohexyl-6-nitro-7-(2-trifluoroacetamidomethyl-1-pyrrolyl)quinoxaline-2,3(1H,4H)-dione 9.1 g (30 mmol) of product 2g and 9.7 g (37.5 mmol) of product 34a were stirred in 250 ml of glacial acetic acid at 100° C. for 2 h. The mixture was then poured into ice-water and the precipitate was filtered off with suction.

Yield: 12.3 g (86%)

$^1$H-NMR (D$_6$-DMSO): δ=1.2–2.0 (8H), 2.3–2.5 (2H), 4.0–4.5 (3H), 6.2 (1H), 6.3 (1H), 6.7 (1H), 7.8 (1H), 7.5 (1H), 9.6 (1H) and ca. 12.5 (1H) ppm.

c) 7-(2-Aminomethyl-1-pyrrolyl)-1-cyclohexyl-6-nitroquinoxaline-2,3(1H,4H)-dione 12.0 g (25 mmol) of product 34b were added to 200 ml of ethanol, 75 ml of 4M sodium hydroxide solution were added, and the mixture was stirred at room temperature for 45 min. The mixture was diluted with water, acidified with 4M hydrochloric acid and then buffered with aqueous sodium bicarbonate solution, and the resulting precipitate was filtered off with suction. The residue was treated with isopropanol/dimethylformamide (2/1) and filtered off with suction.

Yield: 5.5 g (57%); melting point >300° C.

$^1$H-NMR (CD$_3$COOD): δ=1.2–2.0 (10H), 2.5 (2H), 4.1 (1H), 4.2 (2H), 6.3 (1H), 6.5 (1H), 6.8 (1H), 7.9 (1H) and 8.1 (1H) ppm.

N-(1-(1-Cyclohexyl-6-nitroquinoxaline-2,3(1H,4H)-dion-7-yl)-2-pyrrolyl)methyl-N'-phenylurea 1.5 g (4 mmol) of product 34c, 0.52 g (4.4 mmol) of phenyl isocyanate and 1 spatula tip of 4-(N,N-dimethylamino)pyridine were stirred in 25 ml of anhydrous dimethylformamide at 70° C. for 1 h. The mixture was poured into water and extracted with ethyl acetate, and the organic phase was dried and concentrated under reduced pressure. The residue was crystallized from isopropanol.

Yield: 1.5 g (76%); melting point 256° C.

$^1$H-NMR (CD$_3$COOD): δ=1.2–1.9 (8H), 2.5 (2H), 4.3–4.5 (3H), 6.2 (1H), 6.3 (1H), 6.7 (1H), 6.95 (1H); 7.1–7.2 (5H), 7.7 (1H) and 7.9 (1H) ppm.

Example 35

9-(3-(4-Benzyl-1-piperazinyl)methyl-1-pyrrolyl)-1-(2-ethoxycarbonylethyl)benzo[f]quinoxaline-2,3(1H,4H)-dione dihydrochloride

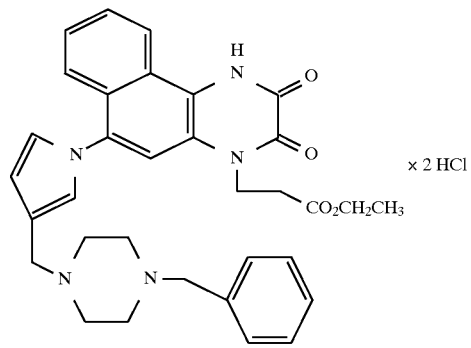

a) N-(1-Nitro-2-naphthyl)-3-aminopropionic acid 150 g (0.74 mol) of 2-methoxy-1-nitronaphthalene, 329 g (3.7 mol) of β-alanine and 255 g (1.8 mol) of potassium carbonate were heated in 1 liter of heating bath fluid (BASF) at 140° C. for 2 h. The mixture was then poured into ice-water and acidified with 4M hydrochloric acid, and the precipitate was filtered off with suction.

Yield: 185 g (97%), melting point 159°–160° C.

$^1$H-NMR (D$_6$-DMSO): 2.7 (2H), 3.7 (2H), 7.2–8.8 (7H) and ca. 12.5 (1H) ppm.

b) Ethyl N-(1-nitro-2-naphthyl)-3-aminopropionate 10 g (38.4 mmol) of product 35a were suspended in 100 ml of ethanol. Then 15 ml of concentrated sulfuric acid were added dropwise, and the mixture was refluxed for 1 h. The solution was subsequently poured into ice-water and extracted with ethyl acetate. The organic phase was dried and concentrated under reduced pressure. The residue was recrystallized from ethanol.

Yield: 7.9 g (72%), melting point 61°–62° C.

$^1$H-NMR (D$_6$-DMSO): δ=1.2 (3H), 2.7 (2H), 3.7 (2H), 4.1 (2H) and 7.3–8.7 (7H) ppm.

c) Ethyl N-(2-ethoxycarbonylethyl)-N-(1-nitro-2-naphthyl) oxamate 4.0 g (13.9 mmol) of product 35b and 3.8 ml (27.7 mmol) of triethylamine were dissolved in 100 ml of anhydrous tetrahydrofuran. At about 0° C., 1.7 ml (15.3 mmol) of ethyl oxalyl chloride dissolved in 20 ml of tetrahydrofuran were added dropwise. The mixture was then stirred at 0° C. for 30 min and subsequently refluxed for 15 min. The mixture was poured into ice-water and extracted with ethyl acetate. The organic phase was washed with aqueous sodium bicarbonate solution, dried and concentrated under reduced pressure.

Yield: 5.4 g (100%)

d) 1-(2-Ethoxycarbonylethyl)benzo[f]quinoxaline-2,3(1H,4H)-dione 240 g (0.62 mol) of product 35c and 80 ml (1 mol) of triethylamine were dissolved in 700 ml of tetrahydrofuran and, after addition of 5 g of palladium/carbon (10%), hydrogenated. The mixture was then filtered and the filtrate was concentrated under reduced pressure. The residue was treated with ethanol and filtered off with suction.

Yield: 94 g (47%), melting point 227°–228° C.

$^1$H-NMR (D$_6$-DMSO): δ=1.2 (3H), 2.7 (2H), 4.1 (2H), 4.5 (2H), 7.4–8.0 (5H), 8.6 (1H) and 12.2 (1H) ppm.

e) 1-(2-Ethoxycarbonylethyl)-9-nitrobenzo[f]quinoxaline-2,3-(1H,4H)-dione 90 g (0.29 mol) of product 35d were dissolved in 1 liter of concentrated acetic acid, and 180 ml of 65% strength nitric acid were added dropwise. The mixture was then stirred at room temperature for about 30 min. The precipitate was filtered off with suction.

Yield: 87.5 g (82%), melting point 230°–231° C.

$^1$H-NMR (D$_6$-DMSO): δ=1.2 (3H), 2.8 (2H), 4.1 (2H), 4.5 (1H), 7.8 (2H), 8.4 (1H), 8.5 (1H), 8.8 (1H) and 12.5 (1H) ppm.

f) 9-Amino-1-(2-ethoxycarbonylethyl)benzo[f]quinoxaline-2,3(1H,4H)-dione 87 g (0.24 mol) of product 35a were dissolved in 1 liter of dimethylformamide and, after addition of 2.5 g of palladium/carbon (10%), hydrogenated. The mixture was then filtered and the filtrate was concentrated under reduced pressure. The residue was treated with ethanol and filtered off with suction.

Yield: 80 g (100%), melting point >250° C.

$^1$H-NMR (D$_6$-DMSO): δ=1.2 (3H), 2.8 (2H), 4.1 (2H), 4.2 (2H), 6.9 (1H), 7.4 (1H), 7.5 (1H), 8.1 (1H), 8.5 (1H) and 12 (1H) ppm.

g) 1-(2-Ethoxycarbonylethyl)-9-(3-formyl-1-pyrrolyl)benzo[f]-quinoxaline-2,3(1H,4H)-dione 10 g (30.6 mmol) of product 35f and 4.9 g (30.6 mmol) of 2,5-dimethoxytetrahydrofuran-3-ylcarbaldehyde were refluxed in 300 ml of glacial acetic acid for 15 min. The mixture was then concentrated under reduced pressure, and the resulting residue was treated with ethanol and filtered off with suction.

Yield: 3.3 g (76%), melting point >250° C.

$^1$H-NMR (D$_6$-DMSO): δ=1.2 (3H), 2.8 (2H), 4.0 (2H), 4.5 (2H), 6.8 (1H), 7.2–8.2 (6H), 8.7 (1H), 9.8 (1H) and ca. 12.5 (1H) ppm.

h) 9-(3-(4-Benzyl-1-piperazinyl)methyl-1-pyrrolyl)-1-(2-ethoxycarbonylethyl)benzo[f]quinoxaline-2,3(1H,4H)-dione dihydrochloride 1.5 g (3.7 mmol) of product 35g, 1.3 g (7.4 mmol) of N-benzylpiperazine and 0.22 g (3.7 mmol) of glacial acetic acid were dissolved in 70 ml of anhydrous dimethylformamide, and 0.23 g (3.7 mmol) of sodium cyanoborohydride was added. The mixture was stirred at room temperature for 72 h. The solution was then poured into aqueous sodium bicarbonate solution and extracted with ethyl acetate. The organic phase was extracted once more with 2M hydrochloric acid. The combined acidic phases were subsequently neutralized with sodium hydroxide solution, whereupon an oil separated out and was dissolved in methylene chloride. This organic phase was dried and concentrated under reduced pressure. The residue was taken up in ether, and ethereal hydrogen chloride solution was added. The precipitated product was filtered off with suction.

Yield: 1.1 g (47%), melting point >180° C. (decomposition).

$^1$H-NMR (D$_6$-DMSO): δ=1.1 (3H), 2.7 (2H), 3.0–3.7 (10H), 4.0 (2H), 4.2–4.4 (2H), 4.5 (2H), 6.6 (1H), 7.2 (1H), 7.3–7.8 (12H), 8.7 (1H), 9.8 (1H) and 12.4 (broad) ppm.

Example 36

9-(3-(4-Benzyl-1-piperazinyl)methyl-1-pyrrolyl)-1-carboxymethylbenzo[f]quinoxaline-2,3(1H,4H)-dione

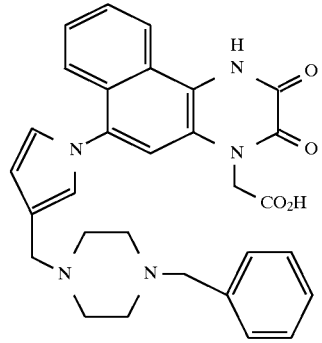

1.0 g (2.65 mmol) of Example 35 was hydrolyzed with lithium hydroxide as in Example 7.

Yield: 0.7 g (50%), melting point >225° C.

$^1$H-NMR (D$_6$-DMSO): δ=2.2 (2H), 2.3–2.6 (4H), 3.2–3.5 (8H), 4.3 (2H), 6.2 (1H), 6.8–7.0 (2H), 7.2–7.5 (9H) and 8.8 (1H) ppm.

Example 37

N-(1-(1-Carboxymethyl-6-trifluoromethylquinoxaline-2,3(1H,4H)-dion-7-yl)-3-pyrrolyl)methyl-N'-phenylurea

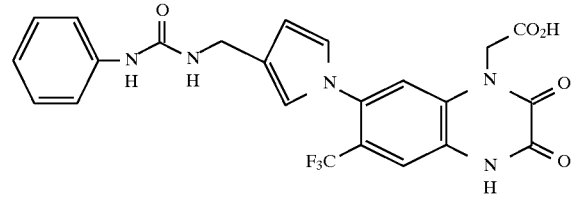

a) Ethyl N-(2-nitro-4-trifluoromethylphenyl)oxamate 51.5 g (0.25 mol) of 2-nitro-4-trifluoromethylaniline, 45 ml (0.32 mol) of triethylamine and 0.1 g of N,N-dimethylaminopyridine were dissolved under a nitrogen atmosphere in 500 ml of anhydrous tetrahydrofuran. At 0°–5° C., 44.4 g (0.32 mol) of ethyl oxalyl chloride were added dropwise. The mixture was then stirred at room temperature until reaction was complete (checked by thin-layer chromatography). The mixture was then concentrated under reduced pressure and the residue was partitioned between water and ethyl acetate. The organic phase was dried and concentrated under reduced pressure. The crude product was recrystallized from ethanol. 68.2 g (89%) of the product were obtained.

$^1$H-NMR (CDCl$_3$): δ=1.5 (3H), 4.5 (2H), 8.0 (1H), 8.6 (1H), 9.05 (1H) and 12.2 (1H) ppm.

b) Ethyl N-(ethoxycarbonylmethyl)-N-(2-nitro-4-trifluormethylphenyl)oxamate 70 g (0.23 mol) of product 37a were dissolved under a nitrogen atmosphere in 1 liter of anhydrous tetrahydrofuran. At room temperature, 34.8 g (0.31 mol) of potassium tert-butanolate were added in portions. The mixture was stirred for 30 min and then 42.1 g (0.25 mol) of ethyl bromoacetate were added dropwise. The mixture was then stirred at room temperature for 2 h and subsequently concentrated under reduced pressure, and the residue was partitioned between ethyl acetate and water. The organic phase was dried and concentrated under reduced pressure. 63 g (70%) of the crude product were obtained and were immediately processed further.

c) 1-(Ethoxycarbonylmethyl)-6-trifluoromethylquinoxaline-2,3(1H,4H)-dione 63 g (0.16 mol) of product 37b were dissolved in 1 liter of acetic acid and heated to reflux. To this were added in portions 54 g (0.97 mol) of iron powder. The mixture was heated for a further 1 h and then cooled and filtered. The filtrate was concentrated under reduced pressure, and the residue was treated with water. The resulting solid was filtered off with suction and recrystallized from ethanol. 48.2 g (95%) of the product were obtained.

Melting point 250°–251° C.
$^1$H-NMR (D$_6$-DMSO): δ=1.25 (3H), 4.7 (2H), 5.0 (2H), 7.5 (3H) and 12.4 (1H) ppm.

d) 1-(Ethoxycarbonylmethyl)-7-nitro-6-trifluoromethylquinoxaline-2,3(1H,4H)-dione 47 g (0.15 mol) of product 37c were dissolved in 500 ml of concentrated sulfuric acid and, at 0° C., 15 g (0.149 mol) of potassium nitrate were added in portions. The mixture was stirred for a further 30 min and then poured into ice-water. The aqueous phase was extracted with ethyl acetate, and the resulting precipitate was filtered off with suction and recrystallized from ethanol. 45.9 g (89%) of the product were obtained.

$^1$H-NMR (D$_6$-DMSO): δ=1.25 (3H), 4.2 (2H), 5.0 (2H), 7.7 (1H), 8.25 (1H) and 12.7 (1H) ppm.

7-Amino-1-(ethoxycarbonylmethyl)-6-trifluoromethylquinoxaline-2,3(1H,4H)-dione 43 g (0.12 mol) of product 37d were dissolved in 300 ml of dimethylformamide and, after addition of 2 g of palladium/carbon (10%), hydrogenated at room temperature under 1 bar. The mixture was then filtered and the filtrate was concentrated under reduced pressure. The residue was treated with ethanol and filtered off with suction. 37.1 g (95%) of the product were obtained.

Melting point >250° C.
$^1$H-NMR (D$_6$-DMSO): δ=1.25 (3H), 4.2 (2H), 4.85 (2H), 5.5 (2H), 6.6 (1H), 7.2 (1H) and 12.0 (1H) ppm.

f) 1-Ethoxycarbonylmethyl-7-(3-trifluoroacetamidomethyl-1-pyrrolyl)-6-trifluoromethylquinoxaline-2,3(1H,4H)-dione 4.0 g (12.1 mmol) of product 37e and 3.1 g (12.1 mmol) of product 4a were refluxed in 75 ml of glacial acetic acid for 10 min. The mixture was then concentrated under reduced pressure, and the residue was treated with ethanol and filtered off with suction.

Yield: 4.8 g (79%), melting point >200° C. (decomposition)
$^1$H-NMR (D$_6$-DMSO): δ=1.2 (3H), 4.2 (2H), 4.3 (2H), 5.0 (2H), 6.2 (1H), 6.8 (2H), 7.5–7.7 (2H), 9.9 (1H) and 12.5 (1H) ppm.

g) 7-(3-Aminomethyl-1-pyrrolyl)-1-carboxymethyl-6-trifluoromethylquinoxaline-2,3(1H,4H)-dione 4.7 g (9.3 mmol) of product 37f were added to 50 ml of tetrahydrofuran, and 75 ml of a 0.5M lithium hydroxide solution were added. The mixture was stirred at room temperature for 1 h. The tetrahydrofuran was then removed under reduced pressure, and the resulting aqueous phase was neutralized with 1M hydrochloric acid. The resulting precipitate was filtered off with suction.

Yield: 3.3 g (94%), melting point >250° C.
$^1$H-NMR (CD$_3$COOD): δ=4.2 (2H), 5.0 (2H), 6.45 (1H), 6.95 (1H), 7.1 (1H), 7.4 (1H) and 7.8 (1H) ppm.

h) N-(1-(1-Carboxymethyl-6-trifluoromethylquinoxaline-2,3(1H,4H)-dion-7-yl)methyl-N'-phenylurea 1.0 g (2.6 mmol) of product 37g and 0.31 g (2.6 mmol) of phenyl isocyanate were heated in 20 ml of anhydrous dimethylformamide at 70° C. for 15 min. The mixture was then concentrated under reduced pressure. The residue was dissolved in ethanol, and the product was then precipitated by addition of ether and was filtered off with suction.

Yield: 1.1 g (84%), melting point >190° C. (decomposition)
$^1$H-NMR (D$_6$-DMSO): δ=4.2 (2H), 4.9 (2H), 6.2 (1H), 6.3 (1H), 6.8–6.9 (2H), 7.1–7.7 (5H), 8.45 (1H) and ca. 12.5 (broad) ppm.

Example 38

N'-Benzyl-N-(1-(1-carboxymethyl-6-trifluoromethylquinoxaline-2,3(1H,4H)-dion-7-yl)-3-pyrrolyl)methylurea

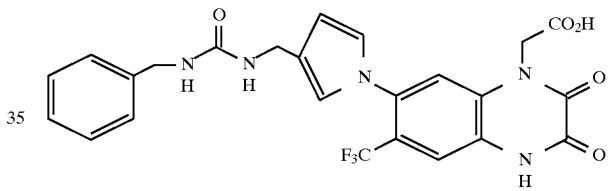

1.0 g (2.6 mmol) of product 37g and 0.35 g (2.6 mmol) of benzyl isocyanate were reacted as for product 37h.

Yield: 1.2 g (89%), melting point 178°–180° C.
$^1$H-NMR (D$_6$-DMSO): δ=4.1 (2H), 4.2 (2H), 4.9 (2H), 6.1 (1H), 6.2 (1H), 6.3 (1H), 6.8 (2H), 7.2–7.7 (7H) and ca. 12.5 (broad) ppm.

Example 39

1-Ethoxycarbonylmethyl-6-nitro-7-(3-(4-(2-phenylethyl)-1-piperazinyl)methyl-1-pyrrolyl)quinoxaline-2,3(1H,4H)-dione

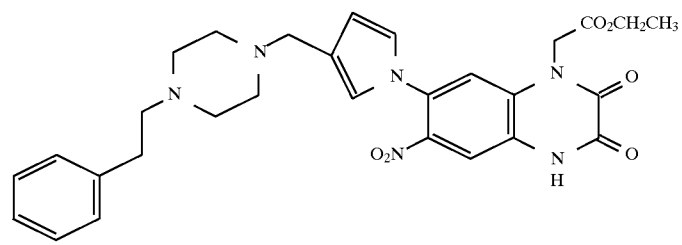

2.0 g (5.2 mmol) of product 5j and 1.97 g (10.4 mmol) of 4-(2-phenylethyl)piperazine were reacted as in method 5k.

Yield: 0.65 g (22%), melting point 124° C.

¹H-NMR (D₆-DMSO): δ=1.2 (3H), 2.4–2.6 (8H), 2.7 (2H), 3.3 (2H), 4.2 (2H), 5.1 (2H), 6.2 (1H), 6.8 (1H), 6.85 (1H), 7.1–7.3 (5H), 7.5 (1H) and 7.8 (1H) ppm.

Example 40

1-Carboxymethyl-6-nitro-7-(3-(4-(2-phenylethyl)-1-piperazinyl)methyl-1-pyrrolyl)quinoxaline-2,3(1H,4H)-dione

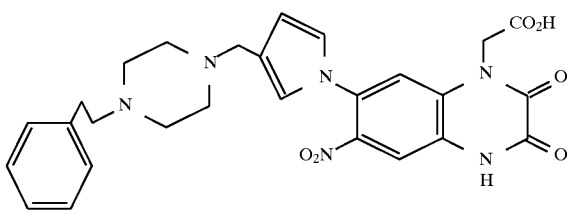

0.6 g (1.1 mmol) of Example 39 were hydrolyzed with lithium hydroxide as in method 1i.

Yield: 0.49 g (86%), melting point >300° C. (decomposition)

1H-NMR (CD₃COOD): δ=3.1 (2H), 3.4 (2H), 3.6–3.9 (6H), 4.3 (2H), 5.1 (2H), 6.4 (1H), 6.9 (1H), 7.1 (1H), 7.2–7.4 (5H), 7.5 (1H) and 8.0 (1H) ppm.

Example 41

1-Ethoxycarbonylmethyl-6-nitro-7-(3-(4-pyridylmethylamido)methyl-1-pyrrolyl)quinoxaline-2,3(1H,4H)-dione

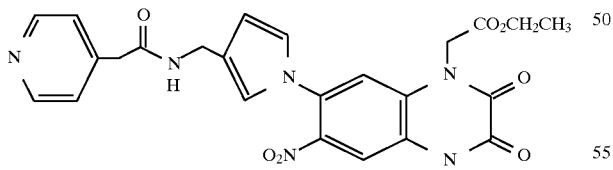

a) 7-(3-Ammoniomethyl-1-pyrrolyl)-1-ethoxycarbonylmethyl-6-nitroquinoxaline-2,3(1H,4H)-dione bisulfate 14 g (20 mmol) of product 10a were added to 250 ml of ethanol and, after addition of 50 ml of 2M sodium hydroxide solution, stirred at room temperature for 5 min. The mixture was then poured onto ice, acidified with 2M hydrochloric acid and subsequently buffered with aqueous sodium bicarbonate solution. The precipitate was filtered off with suction, the filtrate was concentrated under reduced pressure, the residue was extracted with dimethylformamide, and the dimethylformamide solution was concentrated under reduced pressure. This residue was combined with the above precipitate and refluxed in 10% strength ethanolic sulfuric acid for 2 h. The product was filtered off with suction.

Yield: 6.2 g (56%), melting point 122° C.

¹H-NMR (D₆-DMSO): δ=1.2 (3H), 3.9 (2H), 4.1 (2H), 5.0 (2H), 6.4 (1H), 7.0 (1H), 7.1 (1H), 7.5 (1H), 7.9 (1H) ppm.

1-Ethoxycarbonylmethyl-6-nitro-7-(3-(4-pyridylmethylamido)methyl-1-pyrrolyl)quinoxaline-2,3(1H,4H)-dione 0.64 g (4.7 mmol) of 4-pyridylacetic acid were dissolved in 100 ml of anhydrous dimethylformamide, and 0.84 g (5.2 mmol) of 1,1-carbonyldiimidazole was added. The mixture was stirred at room temperature for 30 min and then at 50° C. for a further 30 min. 1.9 g (3.9 mmol) of product 41a which had been suspended in 25 ml of anhydrous dimethylformamide and, after addition of 0.4 g (4 mmol) of triethylamine, had been stirred for 5 min were added, and the mixture was stirred at 80° C. for 1 h. It was subsequently poured into ice-water and the pH was adjusted to 9 by adding aqueous sodium bicarbonate solution. The resulting precipitate was filtered off with suction.

Yield: 1.8 g (89%), melting point >200° C. (decomposition)

¹H-NMR (D₆-DMSO): δ=1.2 (3H), 3.5 (2H), 4.2 (2H), 5.0 (2H), 6.1 (1H), 6.8 (2H), 7.3 (3H), 7.7 (1H) and 8.5 (2H) ppm.

Example 42

N-(1-Ethoxycarbonylmethyl-6-nitroquinoxaline-2,3(1H,4H)-dion-7-yl)-3-pyrrolyl)methyl-N'-(2-(4-pyridyl)ethyl)urea

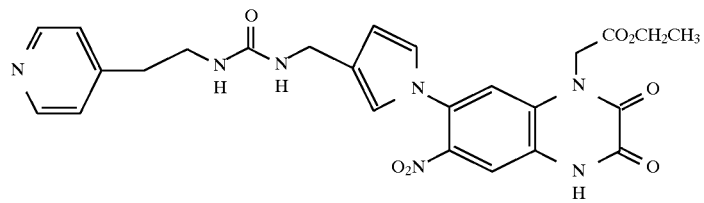

1.9 g (3.9 mmol) of product 41a and 0.48 g (3.9 mmol) of 2-(4-pyridyl)ethylamine were reacted as in method 41b.

Yield: 1.95 g (93%), melting point >200° C. (decomposition)

¹H-NMR (CD₃COOD): δ=1.4 (3H), 3.25 (2H), 3.7 (2H), 4.3 (4H), 5.2 (2H), 6.4 (1H), 6.9 (2H), 7.5 (1H), 8.0 (2H), 8.1 (1H) and 8.9 (2H) ppm.

Example 43

7-(3-(4-Benzyl-1-piperazinyl)methyl-1-pyrrolyl)-1-ethoxycarbonylmethyl-6-trifluoromethylquinoxaline-2,3(1H,4H)-dione

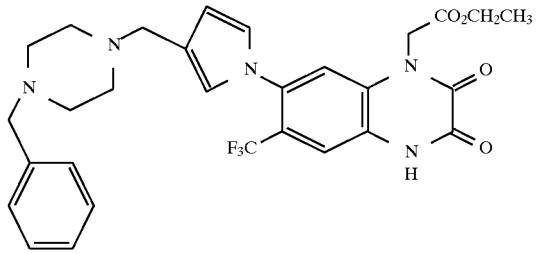

a) 1-(Ethoxycarbonylmethyl)-7-(3-formyl-1-pyrrolyl)-6-trifluoromethylquinoxaline-2,3(1H,4H)-dione 25 g (75.5 mmol) of product 37e and 12 g (75.5 mmol) of 2,5-dimethoxytetrahydrofuran-3-ylcarbaldehyde were heated in 300 ml of acetic acid at 85° C. for 1 h. The mixture was then concentrated under reduced pressure and purified by chromatography on silica gel (mobile phase: methylene chloride/acetone=3/1). 20.3 g (66%) of the product were obtained. Melting point 236°–237° C.

$^1$H-NMR (D$_6$-DMSO): δ=1.2 (3H), 4.2 (2H), 5.0 (2H), 6.6 (1H), 7.05 (1H), 7.65 (1H), 7.8 (2H), 9.8 (1H) and 12.3 (1H) ppm.

7-(3-(4-Benzyl-1-piperazinyl)methyl-1-pyrrolyl)-1-ethoxycarbonylmethyl-6-trifluoromethylquinoxaline-2,3(1H,4H)-dione 1.5 g (3.7 mmol) of product 43a and 1.3 g (7.2 mmol) of 4-benzylpiperazine were reacted as in method 8b.

Yield: 0.98 g (42%), melting point >190° C. (decomposition)

$^1$H-NMR (D$_6$-DMSO): δ=1.2 (3H), 3.2–3.8 (8H), 4.1–4.4 (6H), 5.0 (2H), 6.5 (1H), 7.0 (1H), 7.2 (1H), 7.4–7.8 (7H) and ca. 12.7 (broad) ppm.

Example 44

7-(3-(4-Benzyl-1-piperazinyl)methyl-1-pyrrolyl)-1-carboxymethyl-6-trifluoromethylquinoxaline-2,3(1H,4H)-dione

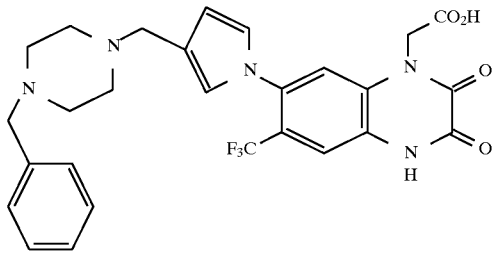

0.9 g (1.4 mmol) of product 43 were hydrolyzed with lithium hydroxide as in Example 7.

Yield: 0.45 g (60%), melting point >245° C. (decomposition)

$^1$H-NMR (CD$_3$COOD): δ=3.5–3.8 (8H), 4.3 (2H), 4.4 (2H), 5.05 (2H), 6.4 (1H), 6.9 (1H), 7.1 (1H), 7.4–7.6 (6H) and 7.7 (1H) ppm.

Example 45

N-(1-(1-Cyclohexyl-6-nitroquinoxaline-2,3(1H,4H)-dion-7-yl)-3-pyrrolyl)methyl-N'-(4-pyridyl)urea

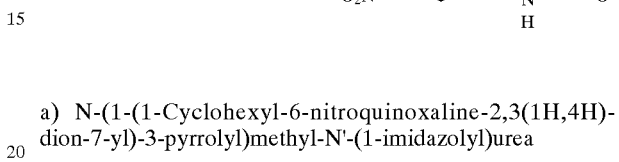

a) N-(1-(1-Cyclohexyl-6-nitroquinoxaline-2,3(1H,4H)-dion-7-yl)-3-pyrrolyl)methyl-N'-(1-imidazolyl)urea 2.0 g (5.2 mmol) of product 2i and 0.92g of 1,1-carbonyldiimidazole were reacted as in method 2j.

Yield: 2.0 g (77%)

b) N-(1-(1-Cyclohexyl-6-nitroquinoxaline-2,3(1H,4H)-dion-7-yl)-3-pyrrolylmethyl-N'-(4-pyridyl)urea 1.7 g (3.6 mmol) of product 45a and 0.34 g (3.6 mmol) of 4-aminopyridine were reacted as in method 2j at 120° C.

Yield: 0.45 g (25%), melting point >240° C. (decomposition)

$^1$H-NMR (D$_6$-DMSO): δ=1.1–1.8 (8H), 2.4 (2H), 4.2 (2H), 4.4 (1H), 6.2 (1H), 6.65 (1H), 7.4 (2H), 7.5 (1H), 7.8 (1H), 8.3 (2H), 9.0 (1H) and ca. 12.5 (broad) ppm.

Example 46

N-(1-(1-Cyclohexyl-6-nitroquinoxaline-2,3(1H,4H)-dion-7-yl)-3pyrrolyl)methyl-N'-phenylthiourea

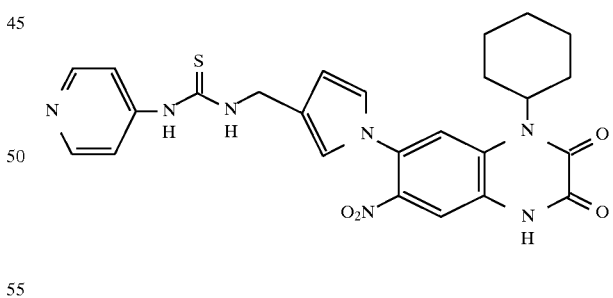

1.0 g (2.6 mmol) of product 2i and 0.35 g (2.8 mmol) of phenyl isothiocyanate were reacted as in method 2j.

Yield: 1.2 g (89%), melting point >210° C. (decomposition)

$^1$H-NMR (CD$_3$COOD): δ=1.1–1.9 (8H), 2.4 (2H), 4.5 (1H), 4.6 (2H), 6.3 (1H), 7.0 (2H), 7.1 (1H), 7.3 (2H), 7.5 (2H), 7.6 (1H), 7.8 (1H), 7.9 (1H), 9.6 (1H) and ca. 12.5 (broad) ppm.

Example 47

6-Nitro-7-(3-(4-(3-trifluoromethylphenyl)-1-piperazinyl)methyl-1-pyrrolyl)quinoxaline-2,3(1H,4H)-dione

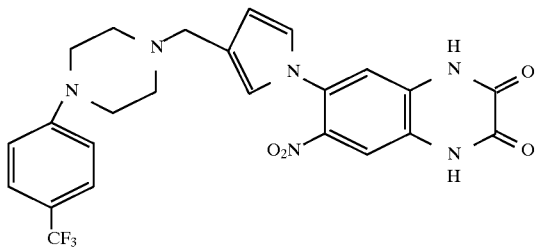

a) 7-(3-Formyl-1-pyrrolyl)-6-nitroquinoxaline-2,3(1H,4H)-dione 2.0 g (9.0 mmol) of product 3c and 1.4 g (9.0 mmol) of 2,5-dimethoxytetrahydrofuran-3-ylcarbaldehyde were refluxed in 50 ml of acetic acid for 1 h. The mixture was subsequently poured into water, and the resulting precipitate was filtered off with suction. This residue was mixed with a little active carbon and silica gel and then boiled in 60 ml of dimethylformamide/tetrahydrofuran (1/5). The suspension was filtered and the filtrate was concentrated under reduced pressure. The residue was suspended in water and filtered off with suction. 0.3 g (13% of theory) of the product was obtained. Melting point >250° C.

$^1$H-NMR (D$_6$-DMSO): δ=6.65 (1H), 7.1 (1H), 7.15 (1H), 7.9 (1H), 7.95 (1H), 9.7 (1H) and ca. 12.3 (broad) ppm.

b) 6-Nitro-7-(3-(4-(3-trifluoromethylphenyl)-1-piperazinyl)methyl-1-pyrrolyl)quinoxaline-2,3(1H,4H)-dione 1.5 g (5 mmol) of product 47a and 2.3 g (10 mmol) of phenylpiperazine were reacted as in method 1j.

Yield: 1.76 g (69%), melting point >300° C.

$^1$H-NMR (D$_6$-DMSO): δ=2.6 (4H), 3.3 (4H), 3.4 (2H), 6.2 (1H), 6.8 (1H), 6.9 (1H), 7.0–7.3 (4H), 7.4 (1H), 7.8 (1H) and ca. 12.3 (broad) ppm.

Example 48

N-(1-(1-(2-carboxyethyl)benzo[f]quinoxaline-2,3(1H,4H)-dion-9-yl)-3-pyrrolyl)methyl-N'-phenylurea

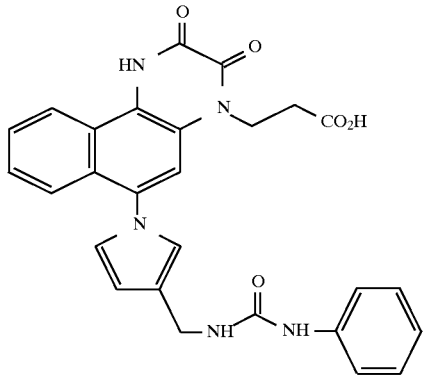

a) 1-(2-Ethoxycarbonylethyl)-9-(3-trifluoroacetamidomethyl-1-pyrrolyl)benzo[f]quinoxaline-2,3(1H,4H)-dione 23 g (70.3 mmol) of product 35f and 18.0 g (70.3 mmol) of product 4a were refluxed in 500 ml of glacial acetic acid for 15 min. The mixture was then poured into ice-water and the resulting precipitate was filtered off with suction.

Yield: 31.8 g (86%), melting point >125° C. (decomposition)

$^1$H-NMR (D$_6$-DMSO): δ=1.2 (3H), 2.7 (2H), 4.0 (2H), 4.4 (2H), 4.5 (2H), 6.3 (1H), 7.1 (2H), 7.5–7.8 (4H), 8.7 (1H), 9.8 (1H) and 12.3 (1H) ppm.

b) 9-(3-Aminomethyl-1-pyrrolyl)-1-(2-carboxyethyl)benzo[f]quinoxaline-2,3(1H,4H)-dione 31.5 g (62.7 mmol) of product 48a were hydrolyzed with lithium hydroxide as in method 31c.

Yield: 20.0 g (85%), melting point >250° C.

$^1$H-NMR (D$_6$-DMSO): δ=3.0 (2H), 4.3 (2H), 4.7 (2H), 6.5 (1H), 7.1 (1H), 7.3 (1H), 7.7–7.9 (4H) and 8.5 (1H) ppm.

c) N-(1-((1-(2-Carboxyethyl)benzo[f]quinoxaline-2,3(1H,4H)-dion-9-yl)-3-pyrrolyl)methyl-N'-phenylurea 3.5 g (9.3 mmol) of product 48b and 1.2 g (10.2 mmol) of phenyl isocyanate were heated in 70 ml of anhydrous dimethylformamide at 120° C. for 30 min. The mixture was then concentrated under reduced pressure, and the residue was purified by chromatography (mobile phase: toluene/tetrahydrofuran/methanol/glacial acetic acid=10/20/10/1).

Yield: 3.0 g (67%), melting point >214° C. (decomposition)

$^1$H-NMR (D$_6$-DMSO): δ=2.6 (2H), 4.2 (2H), 4.5 (2H), 6.2 (1H), 6.5 (1H), 6.8 (1H), 7.0–7.8 (10H), 8.6 (1H), 8.8 (1H) and ca. 12.3 (broad) ppm.

Example 49

N'-Benzyl-N-(1-(1-(2-carboxyethyl)benzo[f]quinoxaline-2,3(1H,4H)-dion-9-yl)-3-pyrrolyl)methylurea

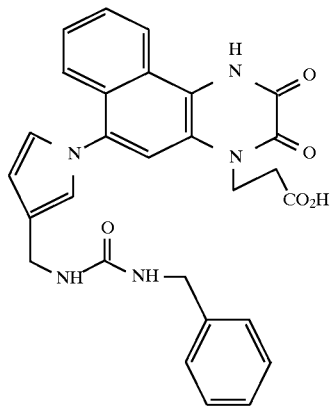

1.6 g (4.2 mmol) of product 48b and 0.62 g (4.7 mmol) of benzyl isocyanate were reacted as in method 48c.

Yield: 2.0 g (93%), melting point >163° C. (decomposition)

$^1$H-NMR (D$_6$-DMSO): δ=2.7 (2H), 4.2 (4H), 4.5 (2H), 6.3 (1H), 6.4 (1H), 6.45 (1H), 7.0 (2H), 7.1 (1H), 7.2–7.4 (5H), 7.5–7.8 (4H), 8.7 (1H) and ca. 12.2 (broad) ppm.

Example 50

N-(1-(1-(2-Carboxyethyl)benzo[f]quinoxaline-2,3(1H,4H)-dion-9-yl)-3-pyrrolyl)methyl-N'-(4-methoxyphenyl)urea

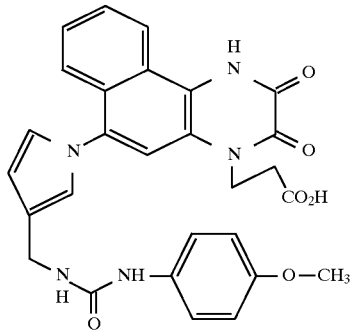

1.5 g (4 mmol) of product 48b and 0.65 g (4.4 mmol) of 4-methoxyphenyl isocyanate were reacted as in method 48c.

Yield: 1.6 g (77%), melting point >240° C.

$^1$H-NMR (D$_6$-DMSO): δ=2.7 (2H), 3.7 (3H), 4.3 (2H), 4.5 (2H), 6.3 (2H), 6.7 (2H), 7.3 (2H), 7.5 (2H), 7.7 (1H), 7.8 (1H), 8.3 (1H), 8.7 (1H) and ca. 12.5 (broad) ppm.

Example 51

N-(1-(1-(2-Carboxyethyl)benzo[f]quinoxaline-2,3(1H,4H)-dion-9-yl)-3-pyrrolyl)methyl-N'-(2-methylphenyl)urea

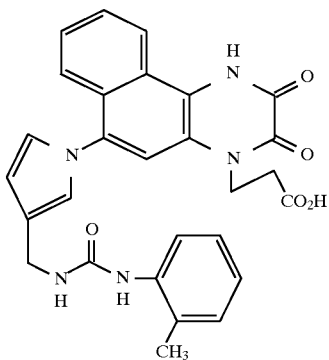

1.5 g (4 mmol) of product 48b and 0.65 g (4.4 mmol) of 2-methylphenyl isocyanate were reacted as in method 49c.

Yield: 1.9 g (94%), melting point >192° C. (decomposition)

$^1$H-NMR (D$_6$-DMSO): δ=2.2 (3H), 2.75 (2H), 4.3 (2H), 4.5 (2H), 6.4 (1H), 6.9 (2H), 7.1 (4H), 7.4–7.8 (6H), 8.7 (1H) and ca. 12.5 (broad) ppm.

Example 52

N-(1-(1-(2-Carboxyethyl)benzo[f]quinoxaline-2,3(1H,4H)-dion-9-yl)-3-pyrrolyl)methyl-N'-(4-nitrophenyl)urea

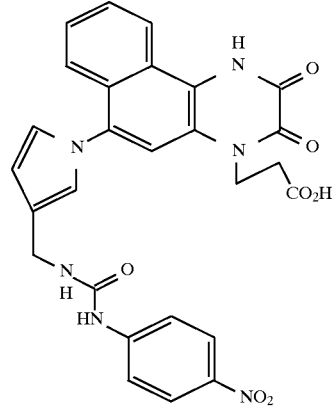

6 g (4.2 mmol) of product 48b and 0.73 g (4.4 mmol) of 4-nitrophenyl isocyanate were reacted as in method 49c.

Yield: 1.9 g (87%), melting point >210° C. (decomposition)

$^1$H-NMR (D$_6$-DMSO): δ=2.6 (2H), 2.75 (3H), 2.9 (3H), 4.3 (2H), 4.5 (2H), 6.3 (1H), 6.7 (1H), 7.1 (2H), 7.5–7.9 (6H), 8.0 (1H), 8.2 (2H), 8.7 (1H), 9.3 (1H) and ca. 12.5 (broad) ppm.

Example 53

N-(1-(1-Cyclohexyl-6-nitroquinoxaline-2,3(1H,4H)-dion-7-yl)-3-pyrrolyl)methyl-N'-phenylguanidine

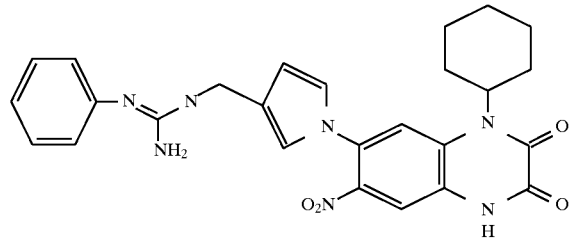

1.9 g (4.8 mmol) of product 2i, 1.4 g (4.8 mmol) of S-methyl-N-phenylisothiourea hydroiodide and a spatula tip of 4-(N,N-dimethylamino)pyridine were refluxed in 50 ml of pyridine for 3 h. The mixture was then poured into water and the precipitate was filtered off with suction.

Yield: 2.0 g (84%), melting point 249° C.

$^1$H-NMR (CD$_3$COOD): δ=1.2–2.0 (8H), 2.6 (2H), ca. 4.5 (3H), 6.4 (1H), 6.8 (1H), 7.0 (1H), 7.3 (3H), 7.4 (2H), 7.7 (1H) and 7.9 (1H) ppm.

Example 54

N-(1-(1-Carboxymethyl-6-trifluoromethylquinoxaline-2,3(1H,4H)-dion-7-yl)-3-pyrrolyl)-3-pyrrolyl)methyl-N'-(3-nitrophenyl)urea

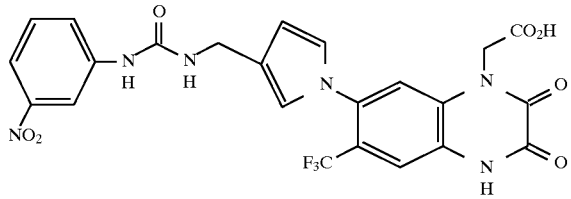

1.2 g (3.1 mmol) of product 37g and 0.57 g (3.4 mmol) of 3-nitrophenyl isocyanate were reacted as in method 37h at 120° C.

Yield: 1.2 g (71%), melting point >200° C. (decomposition)

$^1$H-NMR (D$_6$-DMSO): δ=4.2 (2H), 4.9 (2H), 6.2 (2H), 6.6 (1H), 6.9 (2H), 7.4–7.9 (5H), 8.5 (1H), 9.1 (1H), 12.5 (1H) and ca. 13.5 (broad) ppm.

Example 55

1-Carboxymethyl-6-nitro-7-(3-(4-picolylamidomethyl-1-pyrrolyl)-quinoxaline-2,3(1H,4H)-dione

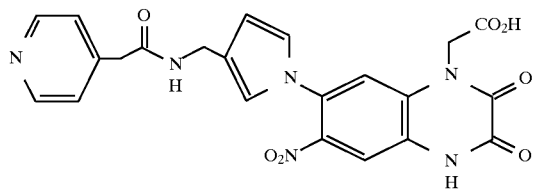

1.6 g (3.2 mmol) of product 41 were hydrolyzed with lithium hydroxide as in method 7.

Yield: 12 g (76%), melting point >300° C.

$^1$H-NMR (D$_6$-DMSO): δ=3.5 (2H), 4.1 (2H), 4.6 (2H), 6.1 (1H), 6.8 (2H), 7.1 (1H), 7.3 (2H), 7.9 (1H), 8.45 (2H), 8.5 (1H) and ca. 12.5 (broad) ppm.

Example 56

N-(1-(1-Carboxymethyl-6-trifluoromethylquinoxaline-2,3(1H,4H)-dion-7-yl)-3-pyrrolyl)methyl-N'-(4-trifluoromethylphenyl)urea

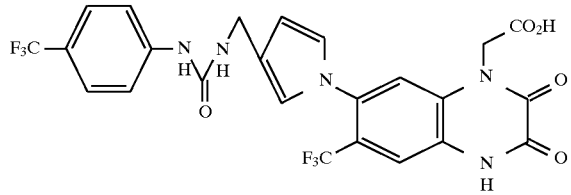

1.6 g (4.2 mmol) of product 37g and 0.8 g (4.2 mmol) of 4-trifluoromethylphenyl isocyanate were reacted as in method 37h at 115° C.

Yield: 1.8 g (83%), melting point >200° C.

$^1$H-NMR (D$_6$-DMSO): δ=4.2 (2H), 5.0 (2H), 6.3 (1H), 6.5 (1H), 6.9 (2H), 7.4–7.8 (4H), 8.9 (1H), 12.5 (1H) and ca. 13.2 (broad) ppm.

Example 57

N'-(4-Bromophenyl)-N-(1-(1-carboxymethyl-6-trifluoromethylquinoxaline-2,3(1H,4H)-dion-3-yl)-3-pyrrolyl)methylurea

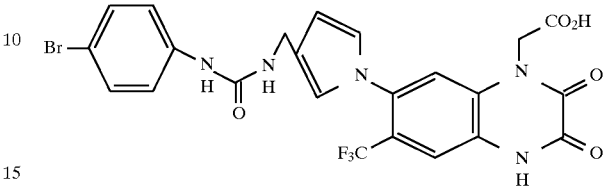

1.2 g (3.1 mmol) of product 37g and 0.62 g (3.1 mmol) of 4-bromophenyl isocyanate were reacted as in method 37h at 120° C.

Yield: 1.8 g (99%), melting point >200° C.

$^1$H-NMR (D$_6$-DMSO): δ=4.2 (2H), 4.9 (2H), 6.2 (1H), 6.4 (1H), 6.9 (2H), 7.3–7.7 (5H), 8.7 (1H) and 12.5 (1H) ppm.

Example 58

N-(1-(1-Carboxymethyl-6-trifluoromethylquinoxaline-2,3(1H,4H)-dion-7-yl)-3-pyrrolyl)methyl-N'-(4-nitriphenyl)urea

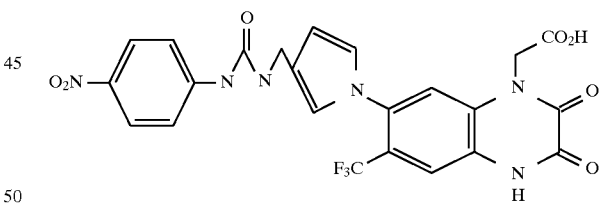

1.0 g (2.6 mmol) of product 37g and 0.48 g (2.9 mmol) of 4-nitrophenyl isocyanate were reacted as in method 37h at 120° C.

Yield: 1.25 g (88%), melting point >220° C. (decomposition)

$^1$H-NMR (D$_6$-DMSO): δ=4.2 (2H), 4.8 (2H), 6.2 (1H), 6.8 (1H), 6.9 (1H), 7.05 (1H), 7.4 (1H), 7.6–7.8 (3H), 8.1 (2H), 10.0 (1H), 12.6 (broad) ppm.

Example 60

N-(1-(1-(2-Carboxyethyl)benzo[f]quinoxaline-2,3 (1H,4H)-dion-9-yl)-3-pyrrolyl)methyl-N'-(4-picolyl) urea

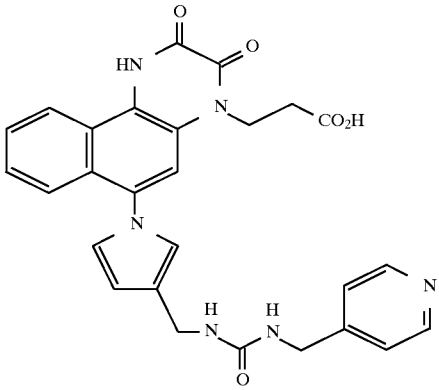

0.64 g (5.9 mmol) of 4-picolylamine and 0.96 g (5.9 mmol) of 1,1-carbonyldiimidazole were stirred in 75 ml of anhydrous dimethylformamide at room temperature for 30 min and at 50° C. 30 min. Then 1.5 g (4 mmol) of product 48b were added and the mixture was heated at 125° C. for 20 min. The mixture was subsequently concentrated under reduced pressure and the residue was treated with dimethylformamide/ethanol and filtered off with suction. The solid was then purified by chromatography (mobile phase: toluene/tetrahydrofuran/methanol/dimethylformamide/glacial acetic acid=16/8/8/8/1).

Yield: 0.5 g (25%), melting point >180° C. (decomposition)

$^1$H-NMR (CD$_3$COOD): δ=3.0 (2H), 4.4 (2H), 4.7 (2H), 4.8 (2H), 6.4 (1H), 7.05 (1H), 7.1 (1H), 7.6 (1H), 7.8 (3H), 7.95 (2H), 8.5 (1H) and 8.8 (2H) ppm.

Example 61

Cis-N-(1-(1-(2-hydroxy-1-cyclohexyl)-6-trifluoromethylquinoxaline-2,3(1H,4H)-dion-7-yl)-3-pyrrolyl)-N'-phenylguanidine

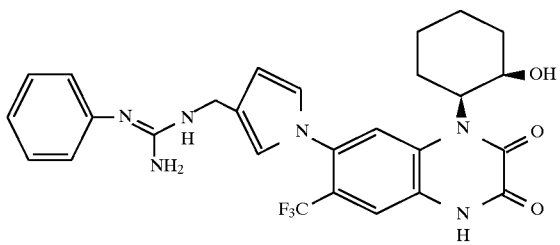

a) 2-(N-(2-Nitro-4-trifluoromethylphenyl)amino) cyclohexanol 44.2 g (0.2 mol) of 4-chloro-3-nitrobenzotrifluoride, 29.7 g of 2-aminocyclohexanol and 54.2 g of potassium carbonate were stirred in 500 ml of dimethylformamide at 100° C. for 2 h. The mixture was then poured into ice-water and the precipitate was filtered off with suction.

Yield: 56.1 g (94%)

$^1$H-NMR (D$_6$-DMSO): δ=1.2–2.2 (8H), 3.5 (2H), 5.0 (1H), 7.3 (1H), 7.7 (1H) and 8.4 (2H) ppm.

b) 4-(2-Acetyloxy-1-cyclohexyl)amino-3-nitrobenzoin fluoride 93.5 g (0.31 mol) of product 61a were dissolved in 1 liter of pyridine and, at 10° C., 30.2 g (0.38 mol) of acetyl chloride were added dropwise. The mixture was then stirred for about 30 min and subsequently concentrated under reduced pressure, and the residue was poured into ice-water. This aqueous phase was extracted with ethyl acetate. The organic phase was subsequently dried and concentrated under reduced pressure. The residue was extracted with hot n-heptane, which was then concentrated under reduced pressure.

Yield: 100.2 g (94%)

$^1$H-NMR (D$_6$-DMSO): δ=1.3–2.1 (11H), 3.9 (1H), 4.9 (1H), 7.4 (1H), 7.8 (1H), 8.2 (1H) and 8.3 (1H) ppm.

c) 4-(2-Acetyloxy-1-cyclohexyl)amino-3-aminobenzotrifluoride 100.2 g (0.29 mol) of product 61c were dissolved in 500 ml of tetrahydrofuran/methanol (1:1) and, after addition of 5 g of palladium/carbon (10%), hydrogenated. The mixture was then filtered and the filtrate was concentrated under reduced pressure.

Yield: 91.6 g (100%)

$^1$H-NMR (D$_6$-DMSO): δ=1.2–2.1 (11H), 3.4 (1H), 4.6–5.0 (3H), 6.7 (1H) and 6.8 (2H) ppm.

d) 1-(2-Acetoxycyclohexyl)-6-trifluoromethylquinoxaline-2,3(1H,4H)-dione 90.4 g (0.29 mol) of product 61c and 43.4 g (0.43 mol) of triethylamine were dissolved in 500 ml of tetrahydrofuran and, at 5°–10° C., 48.7 g (0.36 mol) of ethyl oxalyl chloride dissolved in 50 ml of anhydrous tetrahydrofuran were added dropwise. The mixture was then stirred for 1 h. The precipitate was filtered off with suction and the filtrate was concentrated under reduced pressure. The residue was partitioned between ice-water and ethyl acetate, and the organic phase was dried and concentrated under reduced pressure. The resulting oil was heated in 500 ml of diphenyl ether at 175° C. for about 1.5 h. The mixture was then cooled to 100° C. and 2 l of naphtha were cautiously added. The resulting precipitate was then filtered off with suction at room temperature.

Yield: 75.7 g (72%), melting point 237° C.

$^1$H-NMR (D$_6$-DMSO): δ=1.3–2.2 (11H), 4.6 (1H), 5.7 (1H), 7.4–7.5 (2H), 7.9 (1H) and ca. 12.2 (broad) ppm.

e) Cis-1-(2-acetoxycyclohexyl)-7-nitro-6-trifluoromethylquinoxaline-2,3(1H,4H)-dione 5.0 g (13.5 mmol) of product 61d were dissolved in 100 ml of concentrated sulfuric acid and, at 0° C. 1.4 g (13.5 mmol) of potassium nitrate were added. The mixture was then stirred at 0° C. for 2 h. The mixture was subsequently cautiously poured onto ice, and the aqueous phase was extracted with ethyl acetate. The organic phase was dried and concentrated under reduced pressure. The residue was recrystallized from i-propanol/methanol and the precipitate was filtered off with suction. The mother liquor was then concentrated under reduced pressure. This residue was treated with acetic anhydride and again filtered off with suction. The product was precipitated from the filtrate by adding ether and was filtered off with suction.

Yield: 1.1 g (20%), melting point 277° C.

$^1$H-NMR (D$_6$-DMSO) δ=1.3–2.2 (11H), 4.2 (1H), 4.9 (1H), 7.6 (1H), 9.2 (1H) and ca. 12 (broad) ppm.

f) Cis-1-(2-Acetoxycyclohexyl)-7-amino-6-trifluoromethylquinoxaline-2,3(1H,4H)-dione 15.7 g (38 mmol) of product 61e were added to 300 ml of tetrahydrofuran/methanol (1/1) and, after addition of 1.5 g of palladium/carbon (10%), hydrogenated. The mixture was then filtered and the filtrate was concentrated under reduced pressure.

Yield: 14.5 g (99%)

g) Cis-1-(2-acetoxycyclohexyl)-7-(3-trifluoroacetamidomethyl-1-pyrrolyl)-6-trifluoromethylquinoxaline-2,3(1H,4H)-dione 7.7 g (20 mmol) of product 61f and 7.7 g (30 mmol) of product 4a were heated in 200 ml of glacial acetic acid at 70° C. for 1.5 h and then at 100° C. for 1.5 h. Active carbon was added to the hot reaction mixture, which was then filtered. The filtrate was then poured into ice-water and the resulting precipitate was filtered off with suction.

Yield: 10.1 g (90%), melting point >180° C. (decomposition)

$^1$H-NMR (D$_6$-DMSO): δ=1.3–2.0 (11H), 4.3 (2H), 4.9 (1H), 5.2 (1H), 6.2 (1H), 6.8 (2H), 7.6 (1H), 7.8 (1H), 9.8 (1H) and ca. 12.2 (1H) ppm.

Cis-7-(3-aminomethyl-1-pyrrolyl)-1-(2-hydroxycyclohexyl)-6-trifluoromethylquinoxaline-2,3(1H,4H)-dione 2.0 g (3.6 mmol) were added to 20 ml of ethanol, and 20 ml of 1M sodium hydroxide solution were added. The mixture was stirred at room temperature for 1 h and then neutralized with 1M hydrochloric acid and the ethanol was removed under reduced pressure. The precipitate was filtered off with suction.

Yield: 1.1 g (73%), melting point >220° C. (decomposition)

$^1$H-NMR (D$_6$-DMSO): δ=1.3–1.9 (8H), 2.6 (1H), 4.1 (2H), 4.8 (1H), 5.3 (1H), 6.25 (1H), 6.85 (1H), 6.9 (1H), 7.5 (2H) and 8.2 (1H) ppm.

i) Cis-N-(1-(1-(2-hydroxycyclohexyl)-6-trifluoromethylquinoxaline-2,3(1H,4H)-dion-3-yl)-3-pyrrolylmethyl)-N'-phenylguanidine 0.93 g (2.2 mmol) of product 61h were added to 40 ml of anhydrous pyridine, and 0.65 g (2.2 mmol) of S-methyl-N-phenylisothiourea was added, and then the mixture was refluxed for 1.5 h. It was subsequently filtered and the filtrate was added to water. The precipitate was filtered off with suction.

Yield: 0.69 g (57%), melting point >260° C. (decomposition)

$^1$H-NMR (D$_6$-DMSO): δ=1.3–2.0 (8H), 2.6 (1H), 4.1 (1H), 4.3 (2H), 4.9 (1H), 6.2 (1H), 6.8 (1H), 6.9 (1H), 7.0 (3H), 7.3 (2H), 7.4 (1H) and 8.1 (1H) ppm.

Example 62

Cis-7-(3-(4-benzyl-1-piperazinyl)methyl-1-pyrrolyl)-1-(2-hydroxycyclohexyl)-7-trifluoromethylquinoxaline-2,3(1H,4H)-dione

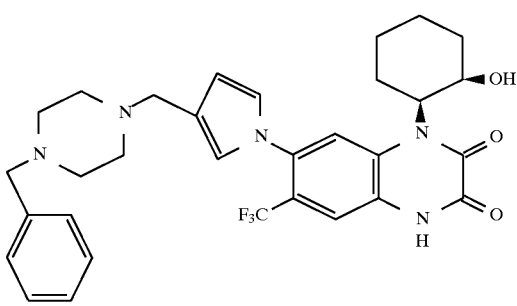

a) Cis-1-(2-acetoxycyclohexyl)-7-(3-formyl-1-pyrrolyl)-6-trifluoromethylquinoxaline-2,3(1H,4H)-dione 1.5 g (4 mmol) of product 61f and 0.8 g (5 mmol) of 2,5-dimethoxytetrahydrofuran-3-ylcarbaldehyde were stirred in 25 ml of glacial acetic acid at 80° C. for 30 min. The mixture was then poured into water and the precipitate was filtered off with suction.

Yield: 1.3 g (71%), melting point >200° C. (decomposition)

$^1$H-NMR (D$_6$-DMSO): δ=1.4–2.0 (11H), 4.8 (1H), 5.2 (1H), 6.7 (1H), 7.1 (1H), 7.6 (1H), 7.9 (2H), 9.8 (1H) and 12.3 (1H) ppm.

b) Cis-7-(3-formyl-1-pyrrolyl)-1-(2-hydroxycyclohexyl)-6-trifluoromethylquinoxaline-2,3(1H,4H)-dione 1.2 g (2.6 mmol) of product 62a were added to 20 ml of methanol, and 10 ml of 2M sodium hydroxide solution were added. The mixture was stirred at room temperature for 45 min and then neutralized with 2M hydrochloric acid, and the alcohol was removed under reduced pressure. The precipitate was filtered off with suction.

Yield: 1.0 g (95%), melting point >246° C. (decomposition)

$^1$H-NMR (D$_6$-DMSO): δ=1.3–2.0 (8H), 2.6 (1H), 4.1 (1H), 4.9 (1H), 5.2 (1H), 6.7 (1H), 7.1 (1H), 7.6 (1H), 7.8 (1H), 8.4 (1H), 9.8 (1H) and 12.3 (1H) ppm.

c) Cis-7-(3-(4-benzyl-1-piperazinyl)methyl-1-pyrrolyl)-1-(2-hydroxycyclohexyl)-7-trifluoromethylquinoxaline-2,3 (1H,4H)-dione 0.9 g (2.1 mmol) of product 62b and 0.75 g (4.3 mmol) of 4-benzylpiperazine were reacted as in method 5h.

Yield: 0.66 g (53%), melting point >300° C.

$^1$H-NMR (CD$_3$COOD): δ=1.4–2.0 (8H), 2.9 (1H), 3.6–3.8 (8H), 4.35 (2H), 4.4 (2H), 4.5 (1H), 4.9 (1H), 6.45 (1H), 6.9 (1H), 7.2 (1H), 7.4–7.6 (5H), 7.6 (1H) and 8.1 (1H) ppm.

Example 63

Cis-N-(1-(1-(2-hydroxycyclohexyl)-6-trifluoromethylquinoxaline-2,3(1H,4H)-dion-7-yl)-3-pyrrolyl)methyl-N'-phenylurea

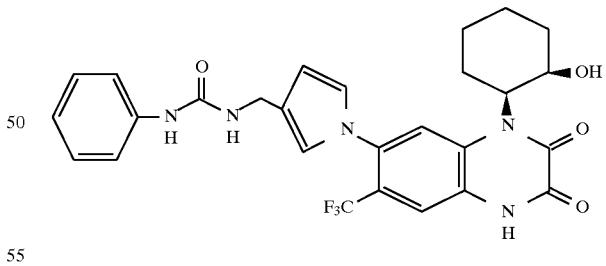

1.0 g (2.4 mmol) of product 61h and 0.28 g (2.4 mmol) of phenyl isocyanate were reacted as in method 2j.

Yield: 0.4 g (31%), melting point >230° C. (decomposition)

$^1$H-NMR (D$_6$-DMSO): δ=1.4–2.0 (8H), 2.6 (1H), 4.1 (1H), 4.2 (2H), 5.9 (1H), 6.2 (1H), 6.3 (1H), 6.9–7.0 (3H), 7.2 (2H), 7.4 (2H), 7.5 (2H), 8.3 (1H), 8.45 (1H) and 12.3 (1H) ppm.

Example 64

Cis-N-(1-(1-(2-hydroxycyclohexyl)-6-trifluoromethylquinoxaline-2,3(1H,4H)-dion-7-yl)-3-pyrrolyl)methyl-N'-(4-nitrophenyl)urea

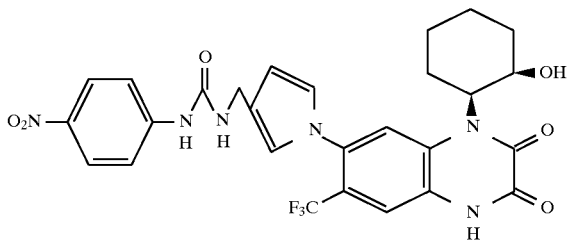

1.0 g (2.4 mmol) of product 61h and 0.39 g (2.4 mmol) of 4-nitrophenyl isocyanate were reacted as in method 2j.

Yield: 0.4 g (27%), melting point >230° C. (decomposition)

$^1$H-NMR (D$_6$-DMSO): δ=1.2–2.0 (8H), 4.1–4.3 (3H), 4.8 (1H), 5.2 (1H), 6.2 (1H), 6.7 (1H), 6.9 (2H), 7.5–7.7 (3H), 8.1 (1H), 8.3 (1H), 9.3 (1H) and ca. 12.3 (broad) ppm.

Example 65

N-(1-(1-(2-Hydroxyethyl)-6-trifluoromethylquinoxaline-2,3(1H,4H)-dion-7-yl)-3-pyrrolyl)methyl-N'-phenylurea

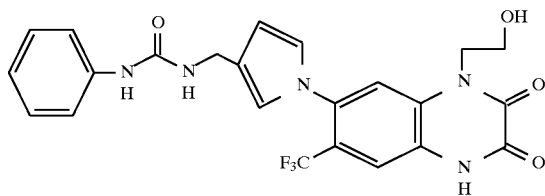

a) 4-(2-Hydroxyethylamino)-3-nitrobenzotrifluoride 112.8 g (0.5 mol) of 4-chloro-3-nitrobenzotrifluoride and 61.1 g (1 mol) of 2-ethanolamine were heated in 500 ml of dimethylformamide at 100° C. for 2 h. The mixture was then concentrated under reduced pressure, and water was added to the residue. The precipitate was filtered off with suction and recrystallized from cyclohexane.

Yield: 116 g (46%), melting point 68°–70° C.

$^1$H-NMR (D$_6$-DMSO): δ=3.5 (2H), 3.7 (2H), 5.0 (1H), 7.3 (1H), 7.8 (1H), 8.3 (1H) and 8.6 (1H) ppm.

b) 3-Amino-4-(2-hydroxyethylamino)benzotrifluoride 115 g (0.46 mol) of product 65a were dissolved in 1 liter of isopropanol, and 11.5 g of palladium/carbon (10%) in 200 ml of water were added. The mixture was heated to 80° C. and then 91 g (1.4 mol) of ammonium formate dissolved in 175 ml of water were rapidly added dropwise. After the reaction was complete, the mixture was filtered and the alcohol was removed from the filtrate under reduced pressure. The resulting precipitate was filtered off with suction, treated with toluene and again filtered off with suction.

Yield: 68.4 g (68%), melting point 92°–94° C.

$^1$H-NMR (D$_6$-DMSO): δ=3.2 (2H), 3.6 (2H), 4.8 (1H), 4.9 (2H), 5.1 (1H), 6.5 (1H) and 8.6 (2H) ppm.

c) 1-(2-Hydroxyethyl)-6-trifluoromethylquinoxaline-2,3(1H,4H)-dione 60 g (0.27 mol) of product 65b were refluxed in 500 ml of ethyl oxalate for 3 h. After cooling, the precipitate was filtered off with suction.

Yield: 55 g (74%), melting point 275°–276° C.

$^1$H-NMR (D$_6$-DMSO): δ=3.7 (2H), 4.2 (2H), 4.9 (1H), 7.4 (1H) and 12.2 (1H) ppm.

d) 1-(2-Hydroxyethyl)-7-nitro-6-trifluoromethylquinoxaline-2,3(1H,4H)-dione 50 g (0.18 mol) of product 65c were dissolved in 500 ml of concentrated sulfuric acid and, at 0° C., 21 g (0.21 mol) of potassium nitrate were added in portions. The mixture was then stirred for 30 min and subsequently poured onto ice and the precipitate was filtered off with suction.

Yield: 25 g (44%), melting point 254°–256° C.

$^1$H-NMR (D$_6$-DMSO): 3.6 (2H), 4.1 (2H), 4.5 (1H), 7.6 (1H), 8.3 (1H) and ca. 12 (broad) ppm.

e) 7-Amino-1-(2-hydroxyethyl)-6-trifluoromethylquinoxaline-2,3(1H,4H)-dione 25 g (78 mmol) of product 65d were reduced with 50 g (0.79 mol) of ammonium formate as in method 65b.

Yield: 13.2 g (58%), melting point 278° C. (decomposition)

$^1$H-NMR (D$_6$-DMSO): δ=3.6 (2H), 4.1 (2H), 4.4 (broad), 5.5 (2H), 6.9 (1H), 7.1 (1H) and 11.8 (broad) ppm.

f) 1-(2-Hydroxyethyl)-7-(3-trifluoroacetamidomethyl-1-pyrrolyl)-6-trifluoromethylquinoxaline-2,3(1H,4H)-dione 5 g (17 mmol) of product 65e and 7.5 g (29 mmol) of product 4a were reacted as in method 4b.

Yield: 7.6 g (96%), melting point 100°–102° C. (decomposition)

$^1$H-NMR (D$_6$-DMSO): δ=3.6 (2H), 4.1–4.4 (4H), 4.8 (1H), 6.2 (1H), 6.9 (2H), 7.5 (2H) and 9.8 (1H) ppm.

g) 7-(3-Aminomethyl-1-pyrrolyl)-1-(2-hydroxyethyl)-6-trifluoromethylquinoxaline-2,3(1H,4H)-dione 7.0 g (15 mmol) of product 65f were hydrolyzed with 1.4 g (59 mmol) of lithium hydroxide as in method 4c.

Yield: 5.3 g (96%)

$^1$H-NMR (D$_6$-DMSO): δ=3.6 (2H), 3.9 (2H), 4.2 (2H), 6.4 (1H), 6.9 (1H), 7.4 (1H) and 7.8 (1H) ppm.

h) N-(1-(1-(2-Hydroxyethyl)-6-trifluoromethylquinoxaline-2,3(1H,4H)-dion-7-yl)-3-pyrrolyl)methyl-N'-phenylurea 1.0 g (2.7 mmol) of product 65g and 0.6 g (5 mmol) of phenyl isocyanate were reacted as in method 4d at 120° C.

Yield: 0.2 g (15%)

$^1$H-NMR (D$_6$-DMSO): δ=3.6 (2H), 4.2 (4H), 6.2 (1H), 6.5 (1H), 6.9 (2H) and 7.2–7.6 (7H) ppm.

Example 66

N-(1-(1-(2-Hydroxyethyl)-6-trifluoromethylquinoxaline-2,3(1H,4H)-dion-7-yl)-3-pyrrolyl)methyl-N'-(4-nitrophenyl)urea

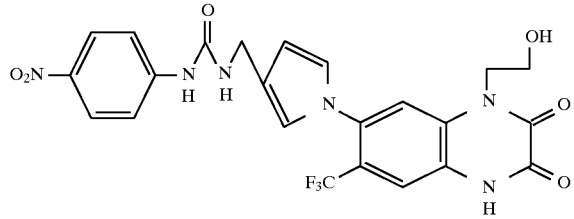

1 g (2.7 mmol) of product 65g and 0.75 g (4.5 mmol) of 4-nitro-phenyl isocyanate were reacted as in method 4d at 120° C.

Yield: 0.1 g (7%)

$^1$H-NMR (D$_6$-DMSO): δ=3.7 (2H), 4.2 (4H), 4.8 (1H), 6.2 (1H), 6.7 (1H), 6.9 (2H), 7.4–7.9 (4H), 8.1 (1H), 8.2 (1H), 9.3 (1H) and ca. 12.3 (broad) ppm.

Example 67

N-(1-(1-Carboxymethyl-6-trifluoromethylquinoxaline-2,3(1H,4H)-dion-7-yl)-3-pyrrolyl)methyl-N'-phenylguanidine

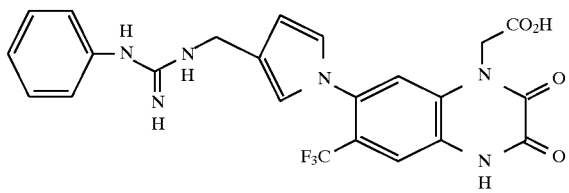

1.5 g (3.9 mmol) of product 37g, 1.2 g (4.0 mmol) of S-methyl-N-phenylisothiourea hydroiodide and a spatula tip of 4-(N,N-dimethylamino)pyridine were heated in 50 ml of pyridine at 100° C. for 3 h. The mixture was then concentrated under reduced pressure and dissolved in a little ethanol. The product was precipitated by adding 10% strength aqueous sodium chloride solution and was filtered off with suction and washed with water. The product was then purified by chromatography (mobile phase: toluene/methanol/tetrahydrofuran/glacial acetic acid=5/5/10/0.1).

Yield: 0.6 g (24%), melting point >230° C.

$^1$H-NMR (D$_6$-DMSO): δ=4.3 (2H), 4.6 (2H), 6.2 (1H), 6.8 (1H), 6.9 (1H), 7.1–7.7 (7H), 8.0 (NH), 9.2 (NH), 11.5 (broad) and 12.4 (broad) ppm.

Example 68

N-(1-(1-Carboxymethylbenzo[f]quinoxaline-2,3(1H,4H)-dion-9-yl)-3-pyrrolyl)methyl-N'-(4-nitrophenyl)urea

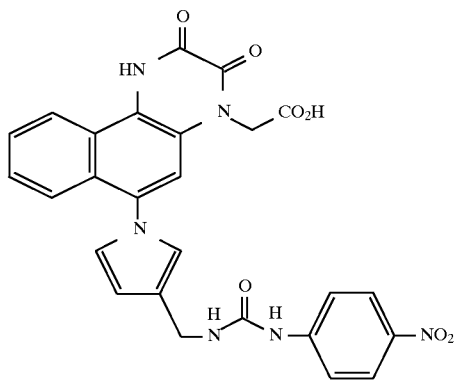

1.0 g (2.7 mmol) of product 31b and 0.45 g (2.75 mmol) of 4-nitrophenyl isocyanate were reacted as in method 31c.

Yield: 0.7 g (49%), melting point >220° C.

$^1$H-NMR (D$_6$-DMSO): δ=4.2 (2H), 5.0 (2H), 6.3 (1H), 6.8 (1H), 7.0 (2H), 7.3–7.7 (6H), 8.0 (2H), 8.7 (1H), 9.4 (1H) and ca. 12.3 (broad) ppm.

Example 69

N-(1-(1-Carboxymethyl-6-trifluoromethylquinoxaline-2,3(1H,4H)-dion-7-yl)-3-pyrrolyl)methyl-N'-(4-nitrophenyl)guanidine

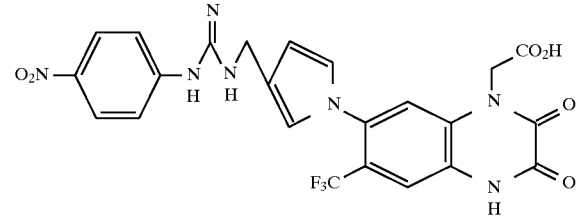

2.0 g (5.2 mmol) of product 37g and 1.95 g (5.8 mmol) of S-methyl-N-(4-nitrophenyl)isothiourea hydroiodide were reacted as in Example 67.

Yield: 1.2 g (43%), melting point >212° C. (decomposition)

$^1$H-NMR (D$_6$-DMSO): δ=4.4 (2H), 5.0 (2H), 6.4 (1H), 6.9 (1H), 7.1 (1H), 7.4 (3H), 7.7 (1H), 8.1–8.6 (3H), 8.8 (1H), 10.7 (1H) and ca. 12.5 (broad) ppm.

Example 70

N-(1-(1-Carboxymethyl-6-nitroquinoxaline-2,3(1H,4H)-dion-7-yl)-3-pyrrolyl)methyl-N'-(2-(4-pyridyl)ethyl)urea 2.1 g (3.9 mmol) of Example 42 were hydrolyzed with 0.28 g (11.7 mmol) of lithium hydroxide as in method 4c.

Yield: 1.4 g (69%), melting point >300° C.

$^1$H-NMR (D$_6$-DMSO): δ=2.7 (2H), 3.3 (2H), 4.0 (2H), 4.9 (2H), 5.9 (1H), 6.1 (1H), 6.2 (2H), 6.8 (1H), 6.9 (1H), 7.2 (2H), 7.4 (1H), 7.8 (1H), 8.4 (2H) and 12.5 (broad) ppm.

Example 71

N-(1-(1-Carboxymethylbenzo[f]quinoxaline-2,3(1H,4H)-dion-9-yl)-3-pyrrolyl)methyl-N'-(4-ethoxycarbonylphenyl)urea

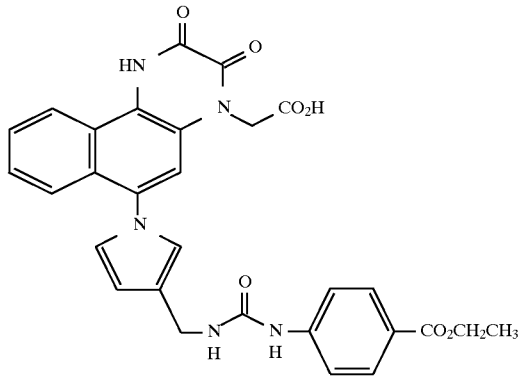

2.0 g (5.5 mmol) of product 31b and 1.0 g (5.5 mmol) of 4-ethoxy-carbonylphenyl isocyanate were reacted as in method 31c at 120° C.

Yield: 2.1 g (71%), melting point >250° C.

$^1$H-NMR (D$_6$-DMSO): δ=1.3 (3H), 4.2 (4H), 4.8 (2H), 6.3 (1H), 6.8–7.1 (3H), 7.3–7.9 (6H), 8.7 (1H), 9.3 (1H) and ca. 12.4 (broad) ppm.

Example 72

N-(1-(1-Carboxymethylbenzo[f]quinoxaline-2,3(1H,4H)-dion-9-yl)-3-pyrrolyl)methyl-N'-(4-carboxyphenyl)urea

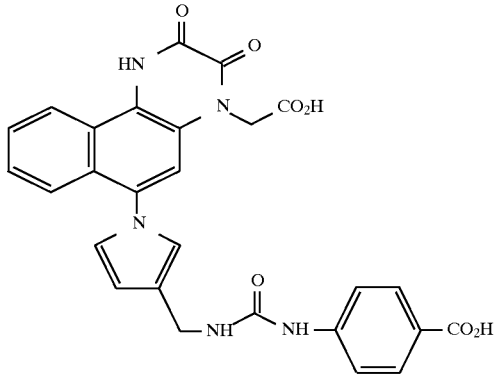

1.0 g (1.8 mmol) of product 71 were hydrolyzed as in method 7.

Yield: 0.6 g (63%)

$^1$H-NMR as dipotassium salt (D$_6$-DMSO): 4.2 (2H), 4.5 (2H), 6.2 (1H), 6.85 (1H), 6.9 (2H), 7.1–7.5 (6), 7.7 (2H), 8.8 (1H) and 8.9 (1H) ppm.

Example 73

N-(1-(1-Carboxymethylbenzo[f]quinoxaline-2,3(1H,4H)-dion-9-yl)pyrrolyl)methyl-N'-(4-nitrophenyl)guanidine

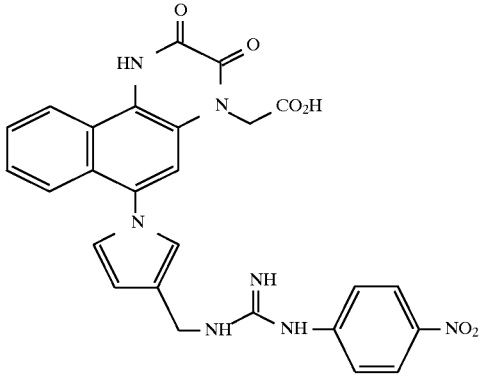

2 g (5.5 mmol) of product 31b and 2 g (6.0 mmol) of S-methyl-N-(4-nitrophenyl)isothiourea hydroiodide were reacted as in Example 67.

Yield: 1.9 g (66%)

$^1$H-NMR (D$_6$-DMSO): δ=4.5 (2H), 5.1 (2H), 6.4 (1H), 7.1 (1H), 7.2 (1H), 7.3–7.9 (5H), 8.2–9.0 (5H), 10.7 (1H), 12.5 (1H) and ca. 13.3 (broad) ppm.

We claim:

1. A quinoxaline-2,3(1H,4H)-dione of the general formula I

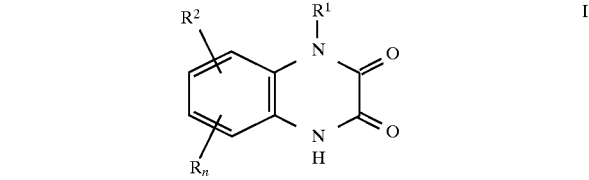

or a tautomer or enantiomer thereof, or a physioligically tolerated salt thereof, wherein, $R^1$ is hydrogen;
a cycloaliphatic radical having up to 8 carbon atoms;
an aliphatic radical having from 1 to 6 carbon atoms which can carry one or two an identical or different substituents selected form the group consisting of phenyl, cyclopentyl, cyclohexyl, —COR$^3$, —CO—O—R$^3$, —CO—NH—R$^3$, —OR$^3$, —CN and

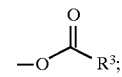

wherein,
where R$^3$ is selected from the group consisting of hydrogen, C$_1$–C$_4$-alkyl, phenyl, benzyl, 1-phenylethyl and 2-phenylethyl;
and where the cycloaliphatic radical or phenyl ring contained in R$^1$ or representing R$^1$ optionally carries up to three identical or different substituents selected from the group consisting of C$_1$–C$_4$-alkyl, C$_1$–C$_4$-haloalkyl, C$_1$–C$_4$-alkoxy, C$_1$–C$_4$-haloalkoxy, halogen, nitro, cyano, —CO—OR$^5$, —CO—NH—R$^5$, —OH, =O and

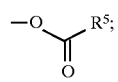

where $R^5$, independently of $R^3$, has the same meanings as $R^3$;

$R^2$ is a pyrrole group:

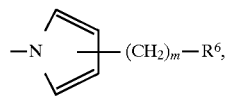

where $R^6$ is a radical selected from the group consisting of

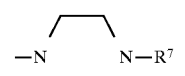

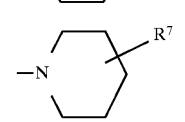

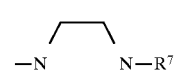

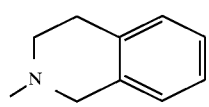

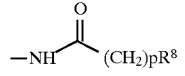

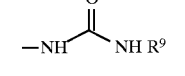

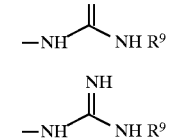

where $R^7$ is hydrogen or branched or linear $C_1$–$C_4$-alkyl which can carry one or two phenyl rings;

$R^8$ is a radical selected from the group consisting of

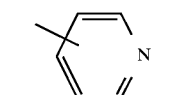

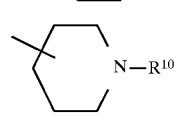

-continued

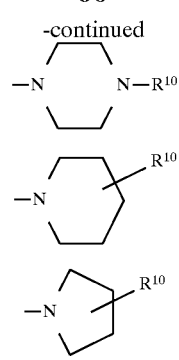

where $R^{10}$ is hydrogen or a branched or linear $C_1$–$C_4$-alkyl which can carry one or two phenyl rings; and $R^9$ is selected from the group consisting of hydrogen, phenyl, a branched or linear $C_1$–$C_4$-alkyl which can carry one or two phenyl rings,

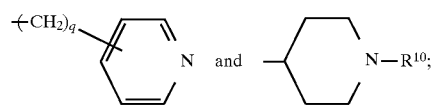

m is an integer from 1 to 4
p and q, independently of one another, are a number from 0 to 4;

where the phenyl groups if present in $R^7$, $R^9$ and $R^{10}$, and in the phenyl rings if representing $R^8$ and $R^9$, can be substituted by a radical selected from the group consisting of halogen, —$NO_2$, —$CF_3$, —CN, —OH, —$OCH_3$, —$NH_2$, —$NHCOCH_3$, —$OCF_3$, —$CO_2$—($C_1$–$C_4$-alkyl), —$CO_2H$, —$CONH_2$, —CONH—($C_1$–$C_4$-alkyl), —$CH_2$—$NHCOCF_3$, —$CH_2NH_2$ and $C_1$–$C_4$-alkyl;

R is a radical selected from the group consisting of $C_1$–$C_4$-alkyl, $C_1$–$C_4$-alkoxy, trifluoromethyl, trichloromethyl, trifluoromethoxy, trichloromethoxy, fluorine, chlorine, bromine, iodine, nitro, cyano and a fused-on benzene ring, said fused-on benzene ring optionally carrying one or two of the radicals selected form the group consisting of $C_1$–$C_4$-alkyl, $C_1$–$C_4$-alkoxy, trifluoromethyl, trichloromethyl, trifluoromethoxy, trichloromethoxy, fluorine, chlorine, bromine, iodine, nitro and cyano; and n is an integer from 0 to 2, or n is 0 or 1 for the fused-on benzene ring.

2. A pharmaceutical composition for topical use, which comprises, per single dose, from 0.1 to 100 mg of a quinoxaline-2,3(1H,4H)-dione I as defined in claim 1, and conventional pharmaceutical ancillary substances.

3. A pharmaceutical composition for topical use, which comprises from 0.0001 to 1% by weight of a quinoxaline-2,3(1H,4H)-dione I as defined in claim 1, and conventional pharmaceutical ancillary substances.

4. A method of treating Parkinson's disease, hypoxia, anoxia, ischemia, epilepsy, anxiety or depression, which comprises administering to a mammal suffering therefrom an effective amount of a quinoxaline-2,3(1H,4H)-dione compound of formula I, as defined in claim 1.

* * * * *